United States Patent
Xia et al.

(10) Patent No.: US 11,976,115 B2
(45) Date of Patent: May 7, 2024

(54) ANTIBODY BINDING TO HUMAN IL-1β, PREPARATION METHOD THEREFOR AND USE THEREOF

(71) Applicant: ZEDA BIOPHARMACEUTICALS, INC., Shenzhen (CN)

(72) Inventors: Yu Xia, Zhongshan (CN); Zhongmin Wang, Zhongshan (CN); Peng Zhang, Zhongshan (CN); Baiyong Li, Zhongshan (CN)

(73) Assignee: ZEDA BIOPHARMACEUTICALS, INC., Shenzhen (CN)

( * ) Notice: Subject to any disclaimer, the term of this patent is extended or adjusted under 35 U.S.C. 154(b) by 608 days.

(21) Appl. No.: 17/292,384

(22) PCT Filed: Nov. 4, 2019

(86) PCT No.: PCT/CN2019/115230
§ 371 (c)(1),
(2) Date: May 7, 2021

(87) PCT Pub. No.: WO2020/093957
PCT Pub. Date: May 14, 2020

(65) Prior Publication Data
US 2022/0064282 A1     Mar. 3, 2022

(30) Foreign Application Priority Data

Nov. 7, 2018 (CN) .......................... 201811322002.7

(51) Int. Cl.
| | | |
|---|---|---|
| *C07K 16/24* | (2006.01) |
| *A61K 39/395* | (2006.01) |
| *A61P 37/00* | (2006.01) |
| *C12N 5/10* | (2006.01) |
| *C12N 15/00* | (2006.01) |
| *C12N 15/13* | (2006.01) |
| *A61K 39/00* | (2006.01) |
| *C12N 5/00* | (2006.01) |
| *C12N 15/09* | (2006.01) |
| *C12N 15/63* | (2006.01) |

(52) U.S. Cl.
CPC ............ *C07K 16/245* (2013.01); *A61P 37/00* (2018.01); *A61K 39/395* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01); *C07K 2317/94* (2013.01); *C12N 5/00* (2013.01); *C12N 15/09* (2013.01); *C12N 15/63* (2013.01); *C12N 2502/99* (2013.01)

(58) Field of Classification Search
CPC ............. C07K 16/245; C07K 2317/24; C07K 2317/33; C07K 2317/565; C07K 2317/76; C07K 2317/92; C07K 2317/94; A61K 2039/505; A61K 39/395; A61P 37/00; A61P 37/06; A61P 19/02; A61P 19/10; C12N 15/09; C12N 15/63; C12N 5/00
See application file for complete search history.

(56) References Cited

FOREIGN PATENT DOCUMENTS

| IN | 106928354 A | 7/2017 |
| WO | 2012034039 A2 | 3/2012 |

*Primary Examiner* — Hong Sang
(74) *Attorney, Agent, or Firm* — Greer, Burns & Crain, Ltd.; Gregory P. Einhorn

(57) ABSTRACT

Provided are antibodies or antigen binding fragments thereof, which can bind to human IL-1β, block the binding of IL-1β to receptors thereof and thereby down regulate the activity of IL-1β, and can be used to prepare drugs for the treatment of immune diseases mediated by IL-1β overexpression such as arthritis, osteoporosis, and tumor necrosis factor receptor-associated periodic syndrome.

14 Claims, 15 Drawing Sheets

Specification includes a Sequence Listing.

SEQUENCE LISTING

<160> NUMBER OF SEQ ID NOS: 38

<210> SEQ ID NO 1
<211> LENGTH: 8
<212> TYPE: PRT
<213> ORGANISM: Mus musculus

<400> SEQUENCE: 1

Gly Tyr Leu Phe Thr Gly Tyr Tyr
1               5

<210> SEQ ID NO 2
<211> LENGTH: 8
<212> TYPE: PRT
<213> ORGANISM: Mus musculus

<400> SEQUENCE: 2

Ile Ser Cys Tyr Asn Gly Asp Thr
1               5

<210> SEQ ID NO 3
<211> LENGTH: 11
<212> TYPE: PRT
<213> ORGANISM: Mus musculus

<400> SEQUENCE: 3

Ser Arg Ser Asp Tyr Tyr Gly Thr Ser Asp Tyr
1               5                   10

<210> SEQ ID NO 4
<211> LENGTH: 5
<212> TYPE: PRT
<213> ORGANISM: Mus musculus

<400> SEQUENCE: 4

Ser Ser Val Ser Tyr
1               5

<210> SEQ ID NO 5
<211> LENGTH: 3
<212> TYPE: PRT
<213> ORGANISM: Mus musculus

<400> SEQUENCE: 5

Thr Thr Ser
1

<210> SEQ ID NO 6
<211> LENGTH: 9
<212> TYPE: PRT
<213> ORGANISM: Mus musculus

<400> SEQUENCE: 6

Gln Gln Arg Ile Ile Tyr Pro Pro Thr
1               5

<210> SEQ ID NO 7
<211> LENGTH: 118
<212> TYPE: PRT
<213> ORGANISM: Mus musculus

<400> SEQUENCE: 7

Glu Val Gln Leu Gln Gln Ser Gly Pro Glu Leu Val Lys Thr Gly Ala
1               5                   10                  15

Ser Val Lys Ile Ser Cys Lys Ala Ser Gly Tyr Leu Phe Thr Gly Tyr
            20                  25                  30

Tyr Met His Trp Val Lys Gln Ser His Gly Lys Ser Leu Glu Trp Ile
        35                  40                  45

Gly Phe Ile Ser Cys Tyr Asn Gly Asp Thr Thr Tyr Asn Gln Lys Phe
    50                  55                  60

Lys Asp Lys Ala Thr Phe Thr Val Asp Thr Ser Ser Asn Thr Ala Tyr
65                  70                  75                  80

Met Gln Phe Asn Ser Leu Thr Ser Glu Asp Ser Ala Val Tyr Tyr Cys
                85                  90                  95

Ser Arg Ser Asp Tyr Tyr Gly Thr Ser Asp Tyr Trp Gly Gln Gly Thr
            100                 105                 110

Thr Leu Thr Val Ser Ser
        115

<210> SEQ ID NO 8

```
<211> LENGTH: 106
<212> TYPE: PRT
<213> ORGANISM: Mus musculus

<400> SEQUENCE: 8

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
                35                  40                  45

Thr Thr Ser Thr Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ile Ile Tyr Pro Pro Thr
                85                  90                  95

Phe Gly Gly Gly Thr Lys Leu Glu Ile Lys
            100                 105

<210> SEQ ID NO 9
<211> LENGTH: 118
<212> TYPE: PRT
<213> ORGANISM: Homo sapiens

<400> SEQUENCE: 9

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Leu Phe Thr Gly Tyr
            20                  25                  30

Tyr Met His Trp Val Lys Gln Ala Pro Gly Lys Gly Leu Glu Trp Ile
                35                  40                  45

Gly Phe Ile Ser Cys Tyr Asn Gly Asp Thr Thr Tyr Asn Gln Lys Phe
50                  55                  60

Gln Gly Lys Ala Thr Phe Thr Val Asp Thr Ser Thr Asn Thr Ala Tyr
65                  70                  75                  80

Met Glu Phe Asn Ser Leu Thr Ser Glu Asp Thr Ala Val Tyr Tyr Cys
                85                  90                  95

Ser Arg Ser Asp Tyr Tyr Gly Ser Asp Tyr Trp Gly Gln Gly Thr
            100                 105                 110

Thr Leu Thr Val Ser Ser
        115

<210> SEQ ID NO 10
<211> LENGTH: 106
<212> TYPE: PRT
<213> ORGANISM: Homo sapiens

<400> SEQUENCE: 10

Glu Ile Val Leu Thr Gln Ser Pro Ala Thr Met Ser Ala Ser Pro Gly
1               5                   10                  15

Glu Arg Val Thr Ile Ser Cys Arg Ala Ser Ser Val Ser Tyr Met
            20                  25                  30

His Trp Phe Gln Gln Lys Pro Gly Gln Ala Pro Arg Leu Trp Ile Tyr
                35                  40                  45

Thr Thr Ser Thr Leu Ala Thr Gly Val Pro Ala Arg Phe Ser Gly Ser
50                  55                  60
```

```
Gly Ser Gly Thr Asp Tyr Thr Leu Thr Ile Ser Arg Met Glu Pro Glu
 65                  70                  75                  80

Asp Ala Ala Thr Tyr Tyr Cys Gln Gln Arg Ile Ile Tyr Pro Pro Thr
                 85                  90                  95

Phe Gly Gly Gly Thr Lys Leu Glu Ile Lys
            100                 105

<210> SEQ ID NO 11
<211> LENGTH: 118
<212> TYPE: PRT
<213> ORGANISM: Homo sapiens

<400> SEQUENCE: 11

Gln Val Gln Leu Val Gln Ser Gly Ala Glu Val Val Lys Pro Gly Ala
  1               5                  10                  15

Ser Val Lys Val Ser Cys Lys Ala Ser Gly Tyr Leu Phe Thr Gly Tyr
                 20                  25                  30

Tyr Met His Trp Val Arg Gln Ala Pro Gly Gln Gly Leu Glu Trp Ile
             35                  40                  45

Gly Phe Ile Ser Cys Tyr Asn Gly Asp Thr Thr Tyr Asn Gln Lys Phe
 50                  55                  60

Gln Gly Arg Ala Thr Phe Thr Val Asp Thr Ser Thr Asn Thr Ala Tyr
 65                  70                  75                  80

Met Glu Phe Ser Ser Leu Thr Ser Glu Asp Thr Ala Val Tyr Tyr Cys
                 85                  90                  95

Ser Arg Ser Asp Tyr Tyr Gly Ser Asp Tyr Trp Gly Gln Gly Thr
            100                 105                 110

Thr Leu Thr Val Ser Ser
        115

<210> SEQ ID NO 12
<211> LENGTH: 106
<212> TYPE: PRT
<213> ORGANISM: Homo sapiens

<400> SEQUENCE: 12

Glu Ile Val Leu Thr Gln Ser Pro Ala Thr Leu Ser Ala Ser Pro Gly
  1               5                  10                  15

Glu Arg Val Thr Ile Ser Cys Arg Ala Ser Ser Ser Val Ser Tyr Leu
                 20                  25                  30

His Trp Tyr Gln Gln Lys Pro Gly Gln Ala Pro Arg Leu Trp Ile Tyr
             35                  40                  45

Thr Thr Ser Thr Leu Ala Thr Gly Val Pro Ala Arg Phe Ser Gly Ser
 50                  55                  60

Gly Ser Gly Thr Asp Tyr Thr Leu Thr Ile Ser Arg Met Glu Pro Glu
 65                  70                  75                  80

Asp Ala Ala Thr Tyr Tyr Cys Gln Gln Arg Ile Ile Tyr Pro Pro Thr
                 85                  90                  95

Phe Gly Gly Gly Thr Lys Leu Glu Ile Lys
            100                 105

<210> SEQ ID NO 13
<211> LENGTH: 118
<212> TYPE: PRT
<213> ORGANISM: Homo sapiens

<400> SEQUENCE: 13

Gln Val Gln Leu Val Gln Ser Gly Ala Glu Val Val Lys Pro Gly Ala
```

```
              1               5                  10                 15
            Ser Val Lys Val Ser Cys Lys Ala Ser Gly Tyr Leu Phe Thr Gly Tyr
                            20                  25                 30

Tyr Met His Trp Val Arg Gln Ala Pro Gly Gln Gly Leu Glu Trp Ile
                        35                  40                 45

Gly Trp Ile Ser Cys Tyr Asn Gly Asp Thr Asn Tyr Ala Gln Lys Phe
                    50                  55                 60

Gln Gly Arg Val Thr Ile Thr Val Asp Thr Ser Thr Asn Thr Ala Tyr
            65                  70                  75                 80

Met Glu Leu Ser Ser Leu Thr Ser Glu Asp Thr Ala Val Tyr Tyr Cys
                            85                  90                 95

Ser Arg Ser Asp Tyr Tyr Gly Thr Ser Asp Tyr Trp Gly Gln Gly Thr
                            100                 105                110

Thr Leu Thr Val Ser Ser
                    115

<210> SEQ ID NO 14
<211> LENGTH: 106
<212> TYPE: PRT
<213> ORGANISM: Homo sapiens

<400> SEQUENCE: 14

Glu Ile Val Leu Thr Gln Ser Pro Ala Thr Leu Ser Ala Ser Pro Gly
            1               5                  10                 15

Glu Arg Ala Thr Ile Ser Cys Arg Ala Ser Ser Ser Val Ser Tyr Leu
                            20                  25                 30

His Trp Tyr Gln Gln Lys Pro Gly Gln Ala Pro Arg Leu Leu Ile Tyr
                        35                  40                 45

Thr Thr Ser Thr Leu Ala Thr Gly Val Pro Ala Arg Phe Ser Gly Ser
                    50                  55                 60

Gly Ser Gly Thr Asp Tyr Thr Leu Thr Ile Ser Arg Leu Glu Pro Glu
            65                  70                  75                 80

Asp Ala Ala Thr Tyr Tyr Cys Gln Gln Arg Ile Ile Tyr Pro Pro Thr
                            85                  90                 95

Phe Gly Gly Gly Thr Lys Leu Glu Ile Lys
                    100                 105

<210> SEQ ID NO 15
<211> LENGTH: 354
<212> TYPE: DNA
<213> ORGANISM: Mus musculus

<400> SEQUENCE: 15
gaagtgcagc tccagcagag cggaccagaa ctggtgaaga ccggagccag cgtgaagatc        60
tcctgcaaag ccagcggcta tctgttcacc ggctactaca tgcattgggt gaagcagagc       120
cacggcaaga gcctcgagtg gatcggcttc atctcctgct acaacggcga caccacctac       180
aaccagaagt tcaaggacaa ggccaccttc accgtggaca ccagcagcaa caccgcctac       240
atgcagttca acagcctgac cagcgaggac agcgccgtgt actattgcag ccggagcgac       300
tactacggca agcgactatt ggggacaggg cacaaccc tgaccgtgtc tagc              354

<210> SEQ ID NO 16
<211> LENGTH: 318
<212> TYPE: DNA
<213> ORGANISM: Mus musculus

<400> SEQUENCE: 16
```

```
cagatcgtgc tgacccagag cccagccatc atgagcgcta gccccggcga gaaagtgacc    60
atcacctgta gcgcctctag cagcgtgtcc tacatgcatt ggttccagca gaagcccggc   120
accagcccaa agctctggat ctacaccacc agcacactgg ccagcggagt gccagctaga   180
ttcagcggaa gcggcagcgg cacatcttat agcctgacca tcagcaggat ggaggccgaa   240
gacgcagcca cctactattg ccagcagcgg atcatctacc ctcctacctt tggcggcggc   300
acaaagctgg agatcaag                                                 318
```

<210> SEQ ID NO 17
<211> LENGTH: 354
<212> TYPE: DNA
<213> ORGANISM: Homo sapiens

<400> SEQUENCE: 17

```
caggtgcagc tggtgcagag cggagcagaa gtggtgaagc aggagccag cgtgaagatc     60 agctgcaaag ccagcggcta tctgttcacc ggctactaca tgcattgggt gaagcaggcc   120
ccaggcaaag gactggagtg gatcgggttc attagctgct acaacggcga caccacctac   180
aaccagaagt tccagggcaa ggccaccttc accgtggata ccagcaccaa caccgcctac   240
atggagttca acagcctgac cagcgaggac accgccgtgt actattgcag ccggagcgac   300
tactacggca agcgactatt tggggccag ggaacaaccc tgaccgtgtc tagc          354
```

<210> SEQ ID NO 18
<211> LENGTH: 318
<212> TYPE: DNA
<213> ORGANISM: Homo sapiens

<400> SEQUENCE: 18

```
gaaatcgtgc tgacccagag cccagctacc atgagcgcct ctccaggaga gagagtgacc     60
atctcttgca gagccagcag cagcgtgtcc tacatgcatt ggttccagca gaagccagga   120
caggccccac gcctctggat ctacacaaca agcaccctgg ccaccggagt gccagctaga   180
ttcagcggaa gcggcagcgg cacagattat accctgacca tcagcaggat ggagccagag   240
gacgcagcca cctactattg ccagcagcgg atcatctacc ctcctacctt tggcggcggc   300
acaaagctgg agatcaag                                                 318
```

<210> SEQ ID NO 19
<211> LENGTH: 354
<212> TYPE: DNA
<213> ORGANISM: Homo sapiens

<400> SEQUENCE: 19

```
caggtgcagc tggtgcagtc aggagcagaa gtggtgaagc ccggagccag cgtgaaagtg     60
tcttgcaagg ccagcggcta tctgttcacc ggatactaca tgcattgggt ccggcaggcc   120
ccaggacagg gactggagtg gatcgggttc attagctgct acaacggcga caccacctac   180
aaccagaagt tccagggcag ggccaccttc acagtggaca ccagcaccaa caccgcctac   240
atggagttca gcagcctgac cagcgaggac acagccgtgt actattgcag ccggagcgac   300
tactacggca agcgactatt tggggccag ggaacaaccc tgaccgtgtc tagc          354
```

<210> SEQ ID NO 20
<211> LENGTH: 318
<212> TYPE: DNA
<213> ORGANISM: Homo sapiens

<400> SEQUENCE: 20

```
gaaatcgtgc tgacccagag cccagctaca ctgagcgcct ctccaggaga gagagtgacc    60
atctcttgca gagccagcag cagcgtgtcc tacctgcatt ggtaccagca gaagcccgga   120
caggccccac gcctctggat ctacaccaca agcaccctgg ccaccggagt gccagctaga   180
ttcagcggaa gcggcagcgg cacagattat accctgacca tcagcaggat ggagccagag   240
gacgcagcca cctactattg ccagcagcgg atcatctacc ctcctacctt tggcggcggc   300
acaaagctgg agatcaag                                                318
```

<210> SEQ ID NO 21
<211> LENGTH: 354
<212> TYPE: DNA
<213> ORGANISM: Homo sapiens

<400> SEQUENCE: 21

```
caggtgcagc tggtgcagtc aggagcagaa gtggtgaagc ccggagccag cgtgaaagtg    60
tcttgcaagg ccagcggcta tctgtttacc ggctactaca tgcattgggt ccggcaggca   120
cccggacagg gcctggagtg gatcggttgg attagctgct acaacggcga caccaactac   180
gcccagaagt tccagggcag ggtgaccatc accgtggaca ccagcaccaa caccgcctac   240
atggagctga gcagcctgac aagcgaggac acagccgtgt actattgcag ccggagcgac   300
tactacggca aagcgactat tggggccag ggaacaaccc tgaccgtgtc tagc          354
```

<210> SEQ ID NO 22
<211> LENGTH: 318
<212> TYPE: DNA
<213> ORGANISM: Homo sapiens

<400> SEQUENCE: 22

```
gaaatcgtgc tgacccagag cccagctaca ctgagcgcct ctccaggaga agagccacc    60
atctcttgca gagccagcag cagcgtgtcc tacctgcatt ggtaccagca gaagcccgga   120
caggctccca gactgctgat ctacaccacc agcaccctgg ctaccggagt gccagccaga   180
ttcagcggaa gcggcagcgg cacagattat accctgacca tcagcagact ggagccagag   240
gacgcagcca cctactattg ccagcagcgg atcatctacc ctcctacctt tggcggcggc   300
acaaagctgg agatcaag                                                318
```

<210> SEQ ID NO 23
<211> LENGTH: 387
<212> TYPE: PRT
<213> ORGANISM: Artificial Sequence
<220> FEATURE:
<223> OTHER INFORMATION: PEPTIDE

<400> SEQUENCE: 23

```
Ala Pro Val Arg Ser Leu Asn Cys Thr Leu Arg Asp Ser Gln Gln Lys
1               5                   10                  15
Ser Leu Val Met Ser Gly Pro Tyr Glu Leu Lys Ala Leu His Leu Gln
            20                  25                  30
Gly Gln Asp Met Glu Gln Gln Val Val Phe Ser Met Ser Phe Val Gln
        35                  40                  45
Gly Glu Glu Ser Asn Asp Lys Ile Pro Val Ala Leu Gly Leu Lys Glu
    50                  55                  60
Lys Asn Leu Tyr Leu Ser Cys Val Leu Lys Asp Asp Lys Pro Thr Leu
65                  70                  75                  80
```

-continued

```
Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gln Asp Ile Thr
    130                 135                 140

Asp Phe Thr Met Gln Phe Val Ser Ser Lys Leu Glu Asn Leu Tyr Phe
145                 150                 155                 160

Gln Gly Thr His Thr Cys Pro Cys Pro Ala Pro Glu Leu Leu Gly
                165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
            195                 200                 205

Glu Asp Pro Glu Val Lys Phe Asn Trp Tyr Val Asp Gly Val Glu Val
    210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
    370                 375                 380

Pro Gly Lys
385

<210> SEQ ID NO 24
<211> LENGTH: 338
<212> TYPE: PRT
<213> ORGANISM: Artificial Sequence
<220> FEATURE:
<223> OTHER INFORMATION: PEPTIDE

<400> SEQUENCE: 24

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
            20                  25                  30

Val Ser Ser Ala Asn Glu Ile Asp Val Arg Pro Cys Pro Leu Asn Pro
        35                  40                  45
```

```
Asn Glu His Lys Gly Thr Ile Thr Trp Tyr Lys Asp Ser Lys Thr
    50              55                  60

Pro Val Ser Thr Glu Gln Ala Ser Arg Ile His Gln His Lys Glu Lys
65              70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
    195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
    275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr His His His His
                325                 330                 335

His His

<210> SEQ ID NO 25
<211> LENGTH: 160
<212> TYPE: PRT
<213> ORGANISM: Artificial Sequence
<220> FEATURE:
<223> OTHER INFORMATION: PEPTIDE

<400> SEQUENCE: 25

Met Ala Pro Val Arg Ser Leu Asn Cys Thr Leu Arg Asp Ser Gln Gln
1               5                   10                  15

Lys Ser Leu Val Met Ser Gly Pro Tyr Glu Leu Lys Ala Leu His Leu
            20                  25                  30

Gln Gly Gln Asp Met Glu Gln Val Val Phe Ser Met Ser Phe Val
            35                  40                  45

Gln Gly Glu Glu Ser Asn Asp Lys Ile Pro Val Ala Leu Gly Leu Lys
    50                  55                  60

Glu Lys Asn Leu Tyr Leu Ser Cys Val Leu Lys Asp Asp Lys Pro Thr
```

```
                65                  70                  75                  80
Leu Gln Leu Glu Ser Val Asp Pro Lys Asn Tyr Pro Lys Lys Lys Met
                85                  90                  95

Glu Lys Arg Phe Val Phe Asn Lys Ile Glu Ile Asn Asn Lys Leu Glu
            100                 105                 110

Phe Glu Ser Ala Gln Phe Pro Asn Trp Tyr Ile Ser Thr Ser Gln Ala
        115                 120                 125

Glu Asn Met Pro Val Phe Leu Gly Gly Thr Lys Gly Gly Gln Asp Ile
    130                 135                 140

Thr Asp Phe Thr Met Gln Phe Val Ser Ser His His His His His His
145                 150                 155                 160

<210> SEQ ID NO 26
<211> LENGTH: 118
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
            85                  90                  95

Ala Arg Asp Leu Arg Thr Gly Pro Phe Asp Tyr Trp Gly Gln Gly Thr
        100                 105                 110

Leu Val Thr Val Ser Ser
        115

<210> SEQ ID NO 27
<211> LENGTH: 330
<212> TYPE: PRT
<213> ORGANISM: Homo sapiens

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 107
<212> TYPE: PRT
<213> ORGANISM: Homo sapiens

<400> SEQUENCE: 28

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
                100                 105

<210> SEQ ID NO 29
<211> LENGTH: 107
<212> TYPE: PRT
<213> ORGANISM: Homo sapiens

<400> SEQUENCE: 29

Arg Thr Val Ala Ala Pro Ser Val Phe Ile Phe Pro Pro Ser Asp Glu
```

```
               1               5                  10                  15
            Gln Leu Lys Ser Gly Thr Ala Ser Val Val Cys Leu Leu Asn Asn Phe
                           20                  25                  30
            Tyr Pro Arg Glu Ala Lys Val Gln Trp Lys Val Asp Asn Ala Leu Gln
                           35                  40                  45
            Ser Gly Asn Ser Gln Glu Ser Val Thr Glu Gln Ser Lys Asp Ser
                50                  55                  60
            Thr Tyr Ser Leu Ser Ser Thr Leu Thr Leu Ser Lys Ala Asp Tyr Glu
            65                  70                  75                  80
            Lys His Lys Val Tyr Ala Cys Glu Val Thr His Gln Gly Leu Ser Ser
                           85                  90                  95
            Pro Val Thr Lys Ser Phe Asn Arg Gly Glu Cys
                          100                 105

<210> SEQ ID NO 30
<211> LENGTH: 121
<212> TYPE: PRT
<213> ORGANISM: Mus musculus

<400> SEQUENCE: 30

Asp Val Gln Leu Val Glu Ser Gly Gly Gly Leu Val Gln Pro Gly Gly
            1               5                  10                  15
            Ser Arg Lys Leu Ser Cys Ala Ala Ser Gly Phe Thr Phe Ser Thr Phe
                           20                  25                  30
            Gly Met His Trp Val Arg Gln Ala Pro Glu Lys Gly Leu Glu Trp Val
                           35                  40                  45
            Ala Tyr Ile Ser Ser Gly Ser Tyr Thr Ile Tyr Tyr Ala Asp Thr Val
                50                  55                  60
            Arg Gly Arg Phe Thr Ile Ser Arg Asp Asn Pro Lys Asn Thr Leu Phe
            65                  70                  75                  80
            Leu Gln Met Thr Ser Leu Arg Ser Glu Asp Thr Ala Met Tyr Tyr Cys
                           85                  90                  95
            Ala Arg Asp Asp Tyr Asp Val Ser Tyr Tyr Ala Met Asp Tyr Trp Gly
                          100                 105                 110
            Gln Gly Thr Ser Val Thr Val Ser Ser
                          115                 120

<210> SEQ ID NO 31
<211> LENGTH: 363
<212> TYPE: DNA
<213> ORGANISM: Mus musculus

<400> SEQUENCE: 31
gatgtgcagc tcgtggaatc aggaggagga ctggtgcagc ccggcggcag cagaaagctg      60
tcttgcgccg ccagcggctt caccttagc accttcggaa tgcattgggt ccggcaggct     120
ccagagaagg gactcgagtg gtggcctac atcagcagcg gcagctacac catctactac     180
gccgacaccg tgcggggaag attcaccatc agccgggaca cccccaagaa caccctgttc     240
ctgcagatga ccagcctgag gagcgaggat accgccatgt actattgcgc cagagacgac     300
tacgacgtgt cctactacgc catggactat tggggacagg gcacaagcgt gacagtgtct     360
agc                                                                  363

<210> SEQ ID NO 32
<211> LENGTH: 112
<212> TYPE: PRT
<213> ORGANISM: Mus musculus
```

<400> SEQUENCE: 32

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Leu Thr Phe Gly Ala Gly Thr Lys Leu Glu Leu Lys
            100                 105                 110

<210> SEQ ID NO 33
<211> LENGTH: 336
<212> TYPE: DNA
<213> ORGANISM: Mus musculus

<400> SEQUENCE: 33
gatatcgtgc tgacccagtc tccagcctct ctggcagtgt ctctgggcca gagagccaca      60
atctcttgca gagcctccga gagcgtggag tactacggca ccagcctcat gcagtggtac     120
cagcagaaac ccggacagcc tcctaagctg ctgatctacg ccgcctctaa cgtggagagc     180
ggagtgccag ccagattcag cggaagcgga agcggcaccg acttcagcct gaacatccac     240
ccagtggagg aggacgacat cgccatgtac ttctgccagc agagcaggaa agtgccctct     300
ctgacctttg gcgccggaac caagctggaa ctgaag                               336

<210> SEQ ID NO 34
<211> LENGTH: 121
<212> TYPE: PRT
<213> ORGANISM: Mus musculus

<400> SEQUENCE: 34

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30

Gly Met His Trp Val Arg Gln Ala Pro Glu Lys Gly Leu Glu Trp Val
        35                  40                  45

Ala Tyr Ile Ser Ser Gly Ser Tyr Thr Thr Tyr Ala Asp Thr Val
    50                  55                  60

Arg Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Asp Tyr Asp Val Ser Asn Tyr Val Met Asp Tyr Trp Gly
            100                 105                 110

Gln Gly Thr Ser Val Thr Val Ser Ser
        115                 120

<210> SEQ ID NO 35
<211> LENGTH: 363

<212> TYPE: DNA
<213> ORGANISM: Mus musculus

<400> SEQUENCE: 35

```
gacgtgcagc tcgtggagtc cggaggaggg ctggtgcagc cggaggaag ccggaagctg      60
tcctgtgccg cctctggctt caccttttct acatttggca tgcactgggt gaggcaggcc     120
ccagagaagg ggctggagtg ggtggcctac atcagctccg gctcttatac acatactat     180
gccgacaccg tgcggggcag attcacaatc agccgggata accctaagaa tacccctgtt     240
ctgcagatga cctccctgag gtctgaggat acagccatgt actattgcgc cgcgacgat     300
tacgacgtgt ctaactacgt gatggattat tgggggcagg gcaccagcgt gacagtgtct     360
agc                                                                  363
```

<210> SEQ ID NO 36
<211> LENGTH: 112
<212> TYPE: PRT
<213> ORGANISM: Mus musculus

<400> SEQUENCE: 36

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Glu Tyr Tyr
            20                  25                  30
Gly Thr Ser Leu Met Gln Trp Tyr Gln Gln Lys Pro Gly Gln Pro Pro
        35                  40                  45
Lys Leu Leu Ile Tyr Ala Ala Ser Asn Val Glu Ser Gly Val Pro Ala
    50                  55                  60
Arg Phe Thr Gly Ser Gly Ser Gly Thr Val Phe Ser Leu Asn Ile His
65                  70                  75                  80
Pro Val Glu Glu Asp Asp Ile Ala Met Tyr Phe Cys Gln Gln Ser Arg
                85                  90                  95
Lys Val Pro Ser Leu Thr Phe Gly Ala Gly Thr Lys Leu Glu Leu Lys
            100                 105                 110
```

<210> SEQ ID NO 37
<211> LENGTH: 336
<212> TYPE: DNA
<213> ORGANISM: Mus musculus

<400> SEQUENCE: 37

```
gatatcgtgc tgacccagtc tccagcctct ctggcagtgt ctctgggcca gagagccaca     60
atctcttgca gagcctccga gagcgtggag tactacggca ccagcctcat gcagtggtac    120
cagcagaaac ccggacagcc tcctaagctg ctgatctacg ccgcctctaa cgtggagagc    180
ggagtgccag ccagattcac aggaagcgga agcggcaccg tattcagcct gaacatccac    240
ccagtggagg aggacgacat cgccatgtac ttctgccagc agagcaggaa agtgccctct    300
ctgacctttg gcgccggaac caagctggaa ctgaag                              336
```

<210> SEQ ID NO 38
<211> LENGTH: 8
<212> TYPE: PRT
<213> ORGANISM: Artificial Sequence
<220> FEATURE:
<223> OTHER INFORMATION: VARIANT

<400> SEQUENCE: 38

Ile Ser Ala Tyr Asn Gly Asp Thr
1               5

ANTIBODY BINDING TO HUMAN IL-1β, PREPARATION METHOD THEREFOR AND USE THEREOF

RELATED APPLICATIONS

This application is a national phase application claiming benefit of priority under 35 U.S.C. § 371 to International (PCT) Patent Application serial number PCT/CN2019/115230, filed Nov. 4, 2019, which claims benefit of priority to Chinese Patent Application No. CN 201811322002.7, filed Nov. 7, 2018. The aforementioned applications are expressly incorporated herein by reference in their entirety and for all purposes.

FIELD OF THE INVENTION

The present invention relates to the field of antibodies, and more particularly, the present invention discloses an antibody that binds to human IL-1β;

The invention also relates to the preparation method and use of the above antibody.

BACKGROUND OF THE INVENTION

Interleukin 1 protein includes interleukin 1α (IL-1α) and interleukin 1β (IL-1β). IL-1β is a multifunctional cytokine that mediates the growth and differentiation of various lymphocytes, and participates in and regulates various inflammatory processes. The secretion level of IL-1β in the body is regulated by the IL-1 family such as IL-1α and IL-1 receptor antagonist (IL-1Ra).

A variety of immune cells, such as macrophages express IL-1α and secrete IL-1β. IL-10 receptors include IL-1 type I receptor (IL-1RI) and IL-1 type II receptor (IL-1RII). Among them, IL-1RI is expressed in almost all nucleated cells, and IL-1β binds to IL-1RI to cause the aggregation of IL-1 receptor (IL-1R) accessory protein (IL-1RAcP) and form a complex, thereby activating the signal pathway; IL-1RII is present both in the form of being expressed on the cell membrane surface and in soluble form in the body. When IL-1β binds to IL-1RII, it will down-regulate the activity of IL-1β.

A variety of studies have shown that overexpression of IL-1 is the main cause of various immune diseases such as cryopyrin protein-related syndrome, tumor necrosis factor receptor-related periodic syndrome, systemic juvenile idiopathic arthritis, and hyperimmunity globulin D syndrome (HIDS)/mevalonate kinase deficiency (MKD), osteoporosis, osteoarthritis and other inflammatory arthritis. In a variety of inflammatory and autoimmune diseases, the level of IL-1 in serum increases with the deterioration and severity of the disease (Pascual V. Allantaz F, et al., Role of interleukin-1 (IL-1) in the pathogenesis of systemic onset juvenile idiopathic arthritis and clinical response to IL-1 blockade. J Exp Med 2005; 201:1479-86). Other studies have shown that IL-10 plays an important role in the differentiation and maturation of TH17 cells (de Jong E. Suddason T. Lord G M. Translational mini-review series on Th17 cells; development of mouse and human T helper 17 cells. Clin Exp Immunol. 2010 February, 159 (2):148-58). Mature TH17 cells can secrete IL-17, which promotes the occurrence of various immune diseases such as psoriasis. Therefore, IL-1β inhibitors can block the IL-1 signaling pathway and play an important role in the treatment of osteoporosis, inflammatory arthritis and other immune diseases.

Therefore, the development of effective anti-IL-1β antibodies to meet the medication needs of patients has always been a problem that people in the field are trying to solve.

SUMMARY OF THE INVENTION

In order to solve the above problem, the inventors of the present invention conducted a large number of experiments, including antigen immunization, hybridoma screening, antibody expression, antibody purification and research of biological activity, finally obtained a series of antibodies that bind to human IL-1βp. The present invention carried out in vivo pharmacological studies on candidate murine antibodies and humanized antibodies. The results showed that murine antibodies 19E4, 18H11, and 9D5 can significantly reduce IL-1β-induced arthritis lesions in mice. The humanized antibody 18H11 H1L1 at a dose of 10 mg/kg can significantly improve the walking behavior and significantly reduce the swelling area of the knee joints of the mice affected limb. Therefore, the antibodies binding to human IL-1β with a novel structure disclosed in the present invention are expected to become potential therapeutic drugs for treating arthritis, osteoporosis, and other immune diseases.

Therefore, the first object of the present invention provides an antibody or antigen-binding fragment thereof that binds to human IL-1β. The antibody comprises; heavy chain complementarity determining regions H-CDR1, H-CDR2, H-CDR3, having the amino acid sequences as shown in SEQ ID NO: 1, SEQ ID NO: 2, and SEQ ID NO: 3, respectively, and light chain complementarity determining regions L-CDR1, L-CDR2, L-CDR3, having the amino acid sequence as shown in SEQ ID NO: 4, SEQ ID NO: 5, and SEQ ID NO: 6, respectively.

Wherein, the antibody that binds to human IL-1β disclosed in the present invention is the murine antibody 18H11, which comprises a heavy chain variable region having the amino acid sequence as shown in SEQ ID NO: 7, and a light chain variable region having the amino acid sequence as shown in SEQ ID NO: 8.

Wherein, the antibody that binds to human IL-1β disclosed in the present invention is the humanized antibody 18H11HIL1, which comprises a heavy chain variable region having the amino acid sequence as shown in SEQ ID NO: 9, and a light chain variable region having the amino acid sequence as shown in SEQ ID NO: 10.

Wherein, the antibody that binds to human IL-1β disclosed in the present invention is the humanized antibody 18H11H2L2, which comprises a heavy chain variable region having the amino acid sequence as shown in SEQ ID NO: 11, and a light chain variable region having the amino acid sequence as shown in SEQ ID NO: 12.

Wherein, the antibody that binds to human IL-1β disclosed in the present invention is the humanized antibody 18H11H3L3, which comprises a heavy chain variable region having the amino acid sequence as shown in SEQ ID NO: 13, and a light chain variable region having the amino acid sequence as shown in SEQ ID NO: 14.

Wherein, the antigen-binding fragment according to the present invention comprises a Fab fragment, a F(ab)'2 fragment, a Fv fragment, a single chain antibody or a single domain antibody.

The second object of the present invention is to provide a nucleic acid molecule encoding the antibody or antigen-binding fragment thereof that binds to human IL-10.

Wherein, the murine antibody 18H11 comprises a nucleotide sequence encoding the heavy chain variable region as shown in SEQ ID NO: 15, and a nucleotide sequence encoding the light chain variable region as shown in SEQ ID NO: 16.

Wherein, the humanized antibody 18H11H1L1 comprises a nucleotide sequence encoding the heavy chain variable region as shown in SEQ ID NO: 17, and a nucleotide sequence encoding the light chain variable region as shown in SEQ ID NO: 18.

Wherein, the humanized antibody 18H11H2L2 comprises a nucleotide sequence encoding the heavy chain variable region as shown in SEQ ID NO: 19, and a nucleotide sequence encoding the light chain variable region as shown in SEQ ID NO: 20.

Wherein, the humanized antibody 18H1 1H3L3 comprises a nucleotide sequence encoding the heavy chain variable region as shown in SEQ ID NO: 21, and a nucleotide sequence encoding the light chain variable region as shown in SEQ ID NO: 22.

The third object of the present invention is to provide an expression vector comprising the above nucleic acid molecule.

The fourth object of the present invention is to provide a host cell comprising the above expression vector.

The fifth object of the present invention is to provide a method for preparing the antibody or antigen-binding fragment thereof that binds to human IL-1β, comprises the following steps of:
a) under expression conditions, culturing the above host cell, to obtain the antibody or antigen-binding fragment thereof that binds to human IL-1β;
b) isolating and purifying the antibody or antigen-binding fragment thereof that binds to human IL-1β of step a).

The sixth object of the present invention is to provide a pharmaceutical composition comprising the antibody or antigen-binding fragment thereof that binds to human IL-1β. The pharmaceutical composition comprises the antibody or antigen-binding fragment thereof that binds to human IL-1β as described in any one of the above and a pharmaceutically acceptable carrier.

The seventh object of the present invention is to provide the use of the antibody or antigen-binding fragment thereof that binds to human IL-1β or of the above pharmaceutical composition. The use is to prepare a medicine for treating various immune diseases caused by overexpression of IL-1β, such as arthritis, osteoporosis or psoriasis. According to a preferred embodiment of the present invention, the use is to prepare a medicine for treating arthritis.

The eighth object of the present invention is to provide an antibody or antigen-binding fragment thereof that binds to human IL-1β, the heavy chain complementarity determining region H-CDR2 of the antibody or antigen-binding fragment includes the C53A mutation. The heavy chain complementarity determining region H-CDR2 of the antibody 18H11-Hu-C53A (IMGT numbering format) is: ISAYNGDT, which has the amino acid sequence as shown in SEQ ID NO: 38.

The present invention also provides an epitope of human IL-1β that the above antibody binds to: the main binding epitope includes tryptophan (W) at position 120 and isoleucine (I) at position 122 of SEQ ID NO: 23, then phenylalanine (F) at position 112, serine (S) at position 123, and threonine (T) at position 124.

Beneficial Effects

1. The antibodies that bind to human IL-1β screened and obtained by the present invention can specifically bind to human IL-1β. The ELISA results show that the $EC_{50}$ of the murine antibody 18H11 is equivalent to that of the positive control antibody, and the $EC_{50}$ of the humanized antibody 18H11H1L1 is better than that of the positive control antibody.
2. The antibodies that bind to human IL-1β screened and obtained by the present invention can effectively block the binding of IL-1β to its related receptors. Among them, the $EC_{50}$ of the murine antibody 18H11 and the humanized antibody 18H11H1L1 are equivalent to that of the positive control antibody.
3. The antibodies that bind to human IL-1β screened and obtained by the present invention can effectively inhibit 1L-10-induced IL-6 secretion in MRC-5 cells. Among them, the murine antibody 18H11 and the humanized antibody 18H11H1L1 has better effect on inhibiting IL-1β-induced IL-6 secretion in MRC-5 cells than the positive control antibody.
4. The antibody 18H1H1L1 that binds to human IL-1β screened and obtained by the present invention has an equivalent antibody affinity, compared to the positive control antibody, by Fortebio Kinetics analysis.
5. The antibodies that bind to human IL-1β screened and obtained by the present invention can significantly reduce IL-1β-induced arthritis in mice. Among them, the murine antibody 18H11 and the humanized antibody 18H11H1L1 have equivalent therapeutic effects in terms of mouse behavior scoring, joint swelling effect/knee joint area and weight effect, compared to the positive control antibody.
6. The mutant antibody 18H11-Hu-C53A obtained by the present invention, using the heavy chain of 18H11 H1L1 as a template and containing the C53A site in the H-CDR2, has better thermal stability than the wild-type antibody.

In the present invention, the terms "antibody (Ab)" and "immunoglobulin G (IgG)" are heterotetrameric glycoproteins of about 150,000 daltons with identical structural characteristics, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable region (VH) followed by constant regions. Each light chain has a variable region at one end (VL) and a constant region at its other end; the constant region of the light chain is aligned with the first constant region of the heavy chain, and the light chain variable region is aligned with the variable region of the heavy chain. The antibodies of the present invention may be monoclonal antibodies, polyclonal antibodies, multispecific antibodies (such as bispecific antibodies) formed by at least two antibodies, antigen-binding fragments of antibodies, etc. The antibodies of the present invention comprise murine antibodies, chimeric antibodies, humanized antibodies, etc.

In the present invention, the term "monoclonal antibody (mAb)" refers to an antibody obtained from a population of substantially homogeneous antibodies, that is, the individual antibodies contained in the population are the same, except for a few possible naturally occurring mutations. Monoclonal antibodies target a single antigen site with high specificity. Moreover, unlike conventional polyclonal antibody preparations (usually with different antibodies directed against different determinants), each monoclonal antibody is directed against a single determinant on the antigen. In addition to their specificity, the benefit of monoclonal antibodies is that they are synthesized by hybridoma culture and are not contaminated by other immunoglobulins. The modifier "monoclonal" indicates the characteristics of an antibody, which is obtained from a substantially uniform antibody population, and it should not be interpreted as requiring any special method to produce antibodies.

In the present invention, the term "murine antibody" refers to an antibody derived from rats or mice, preferably mice. The murine antibody of the present invention is obtained by immunizing mice with human IL-1β as an antigen and screening hybridoma cells. More preferably, the murine antibodies of the present invention include 19E4, 18H11, and 9D5. Most preferably, the murine antibody of the present invention is 18H11.

In the present invention, the term "humanized antibody" refers to an antibody or antibody fragment obtained by replacing all or part of the CDR region of a human immunoglobulin (acceptor antibody) with a CDR region of a non-human antibody (donor antibody), wherein the donor antibody can be a non-human (for example, mouse, rat or rabbit) antibody with the expected specificity, affinity or reactivity. In addition, some amino acid residues in the framework region (FR) of the acceptor antibody can also be replaced by corresponding non-human antibody amino acid residues, or replaced by other antibody amino acid residues, to further improve or optimize the performance of the antibody. For more details about humanized antibodies, see, for example, Jones et al., Nature, 321:522 525 (1986); Reichmann et al., Nature, 332:323 329 (1988); Presta, Curr. Op. Struct. Biol., 2:593 596 (1992); and Clark, Immunol. Today 21: 397 402 (2000). Preferably, the humanized antibody of the present invention is recombined from the CDR region of the murine antibody 18H11 and the non-CDR region derived from the human antibody. More preferably, the humanized antibody of the present invention includes 18H11 H1L1, 18H11 H2L2 and 18H11 H3L3. Most preferably, the humanized antibody of the present invention is 18H11 H1L1.

In the present invention, the term "variable" refers to the fact that certain portions of the variable regions differ extensively in sequence among antibodies and are responsible for the binding specificity of each particular antibody for its particular antigen. However, the variability is not evenly distributed through the variable regions of antibodies. It is concentrated in three segments called complementarity determining regions (CDRs) or hypervariable regions both in the light chain and the heavy chain variable regions. The more highly conserved portions of the variable regions are called the framework regions (FR). The variable regions of native heavy and light chains each comprise four FR regions, largely adopting a 0-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen binding site of antibodies (see Kabat et al., NIH Publ. No. 91-3242, Volume 1, Pages 647-669 (1991)). The constant regions are not involved directly in binding an antibody to an antigen, but they exhibit various effector functions, such as participation in antibody-dependent cell-mediated cytotoxicity (ADCC).

In the present invention, the term "antigen-binding fragment" refers to a fragment of an antibody capable of specifically binding to an epitope of human IL-1β. Examples of the antigen-binding fragments of the present invention include Fab fragments, F(ab')2 fragments, Fv fragments, single chain antibodies (scFv), single domain antibodies (sdAb), etc. An Fab fragment is a fragment produced by digesting an antibody with papain. An F(ab')2 fragment is a fragment produced by digesting an antibody with pepsin. An Fv fragment is composed of dimers in which the heavy chain variable region and the light chain variable region of an antibody are closely and non-covalently linked. A single-chain antibody (scFv) is an antibody in which the heavy chain variable region and the light chain variable region of an antibody are linked by a short peptide (linker) of 15-20 amino acids. A single domain antibody (sdAb), also called nanobody or heavy chain antibody, is composed of heavy chain only, and its antigen binding region is only a single domain linked to the Fc region through a hinge region.

In the present invention, the terms "binding" and "specific binding" refer to the non-random binding reaction between two molecules, such as the reaction between an antibody and its targeted antigen. Generally, the antibody binds to the antigen with an equilibrium dissociation constant (KD) of less than about $10^{-7}$ M, for example, less than about $10^{-8}$ M, $10^{-9}$M, $10^{-10}$M, $10^{-11}$ M, or less. In the present invention, the term "KD" refers to the equilibrium dissociation constant of a specific antibody-antigen interaction, which is used to describe the binding affinity between the antibody and the antigen. The smaller the equilibrium dissociation constant is, the tighter the antibody-antigen binding is, and the higher the affinity between the antibody and the antigen is. For example, surface plasmon resonance (abbreviated as SPR) is used to measure the binding affinity of antibody to antigen in BIACORE instrument or ELISA is used to measure the relative binding affinity of antibody to antigen.

In the present invention, the terms "epitope" and "human IL-1β epitope" refer to regions located on human IL-1β and related to antibody specific binding.

In the present invention, the term "expression vector" may be pTT5, pSECtag series, pCGS3 series, pCDNA series vectors, etc., as well as other vectors used in mammalian expression systems, etc. The expression vector comprises a fusion DNA sequence connected with appropriate transcription and translation regulatory sequences.

In the present invention, the term "host cell" refers to a cell suitable for expressing the expression vector as described above, which may be a eukaryotic cell, for example, mammalian or insect host cell culture system may be used to express the fusion protein of the present invention, CHO (Chinese hamster Ovary), HEK293, COS, BHK, etc. as well as derived cells of the above-mentioned cells are applicable to the present invention.

In the present invention, the terms "cell" and "cell line" may be used interchangeably.

In the present invention, the term "pharmaceutical composition" means that the antibody that binds to human IL-1β of the present invention can be combined with a pharmaceutically acceptable carrier to form a pharmaceutical preparation composition, so as to exert a therapeutic effect more stably. These preparations can ensure the conformational integrity of the amino acid core sequences of the antibody that binds to human IL-1β disclosed in the present invention, and meanwhile, protect the multifunctional groups of the protein from degradation (including but not limited to aggregation, deamination or oxidation).

In the present invention, the term "IL-1β overexpression disease" means that the expression level of IL-1β in cells in an abnormal disease state is higher than the expression level of IL-1β in normal cells of the same tissue type. The IL-1β overexpression diseases of the present invention include, but are not limited to, various immune diseases such as osteoporosis, osteoarthritis and other inflammatory arthritis, psoriasis and the like.

The following examples are used to further illustrate the present invention and should not be construed as limiting the present invention. The examples do not include a detailed description of traditional methods, such as those methods of constructing expression vectors and preparing plasmids, methods of inserting genes encoding proteins into such vectors and plasmids, or methods of transfecting plasmids into host cells. Such methods are well known to those of ordinary skill in the art, and are described in many publications, including Sambrook, J., Fritsch. E. F. and Maniais, T. (1989) Molecular Cloning: A Laboratory Manual, 2nd edition, Cold spring Harbor Laboratory Press.

In this disclosure, the meanings of abbreviations are explained as follows:

| | | |
|---|---|---|
| IL-1α | Interleukin-1 alpha | Interleukin 1α |
| IL-1β/IL-1b | Interleukin-1 beta | Interleukin 1 beta |
| IL-1R | Interleukin-1 receptor | Interleukin 1 receptor |
| IL-1RI | Interleukin-1 receptor, type I | Interleukin 1 receptor, type I |
| IL-1RII | Interleukin-1 receptor, type II | Interleukin 1 receptor, type II |
| IL-1Ra | Interleukin-1 receptor antagonist | Interleukin 1 type I receptor antagonist |
| IL-1RAcP | Interleukin 1 receptor accessory protein | Interleukin 1 type I receptor accessory protein |
| IL-6 | Interleukin-6 | Interleukin-6 |
| PcAb | Positive control antibody | Positive control antibody |
| PBS | Phosphate buffer saline | Phosphate buffer saline |
| CDNA | Complementary deoxyribonucleic acid | Complementary deoxyribonucleic acid |
| SDS-PAGE | Polyacrylamide gel electrophoresis | Polyacrylamide gel electrophoresis |
| ELISA | Enzyme-linked immunosorbent assay | Enzyme-linked immunosorbent assay |
| $EC_{50}$ | Median effective concentration | Median effective concentration |

DESCRIPTION OF THE FIGURES

FIG. 24 shows the affinity of 18H11-Hu-C53A to IL-1β-A1-F99-His and IL-1β-A1-W120-His;

FIG. 25 shows the binding ability of 18H11-Hu-C53A to amino acids at positions 111-115;

FIG. 26 shows the binding ability of 18H11-Hu-C53A to amino acids at positions 116-120;

FIG. 27 shows the binding ability of 18H11-Hu-C53A to amino acids at positions 120-124.

DETAILED DESCRIPTION OF THE EMBODIMENTS

Example 1 Preparation of Antigen and Candidate Antibody 1.1 Preparation of IL1β-hFc and IL1RI-his (1) The amino acid sequence of human IL11-beta (NCBI Reference Sequence: NP_000567.1) and TEV-hIgG1Fc (hFc: Ig gamma-1 chain C region. ACCESSION: P01857, 106-330) were subjected to fusion design as follows (IL1b-TEV-hIgG1Fc):

```
Amino acid sequence:
                                         (SEQ ID NO: 23)
APVRSLNCTLRDSQQKSLVMSGPYELKALHLQGQDMEQQVVFSMSFVQGE

ESNDKIPVALGLKEKNLYLSCVLKDDKPTLQLESVDPKNYPKKKMEKRFV

FNKIEINNKLEFESAQFPNWYISTSQAENMPVFLGGTKGGQDITDFTMQF

VSSKLENLYFQGTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSKL

TVDKSRWQQGNVFSCSVMHEALHNHYTQKSLSLSPGK
```

Wherein, ENLYFQG is the recognition site for TEV enzyme digestion.

(2) The amino acid sequence of human IL1RI (1-332) (NCBI Reference Sequence: NP_000868.1) and His X6 tag were subjected to fusion design as follows (IL1RI (1-332)-His):

```
Amino acid sequence:
                                         (SEQ ID NO: 24)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYWKWNGSVIDEDDPVLGEDYYSVENPANKRRSTLITVLNISE

IESRFYKHPFTCFAKNTHGIDAAYIQLIYPVTHHHHHH
```

(3) The amino acid sequences corresponding to the above-designed fusion proteins (IL1b-TEV-hIgG1Fc and IL1RT(1-332)-His) were subjected to manual codon optimization (a signal peptide should be added to the N-terminus of IL1b-TEV-hIgG1Fc), and the optimized DNAs were synthesized by GenScript and cloned into a pUC57simple (provided by GenScript) vector to obtain pUC57simple-IL1b-TEV-hIgG1Fc and pUC57simple-IL1RI (1-332)-His plasmids.

(4) After restriction endonuclease digestion (Xba I and BamH I) of the above two plasmids, the gene fragments IL1b-TEV-hIgG11Fc and IL1RI (1-332)-His were recovered by electrophoresis, and ligated with pcDNA3.1 linearized vector (XbaI&BamHI) and recombinantly constructed to obtain pcDNA3.1-IL1b-TEV-hIgG1Fc and pcDNA3.1-IL1RI (1-332)-His plasmids, respectively.

(5) 7 days after the two recombinant plasmids constructed above were transfected into FreeStyle™ 293-F Cells cells (Invitrogen), respectively, the culture solutions were centrifuged at a high speed (4000 rpm for 20 min), vacuum filtered through a microporous filter membrane (0.45 μm microporous filter membrane), and purified using Protein A column and Ni column (protein purification liquid chromatography system/AKTA Purifier 10, GE) according to the operating method provided by the manufacturer, to obtain purified IL1b-TEV-hIgG1Fc and IL1RI (1-332)-His fusion proteins.

Figure 1:
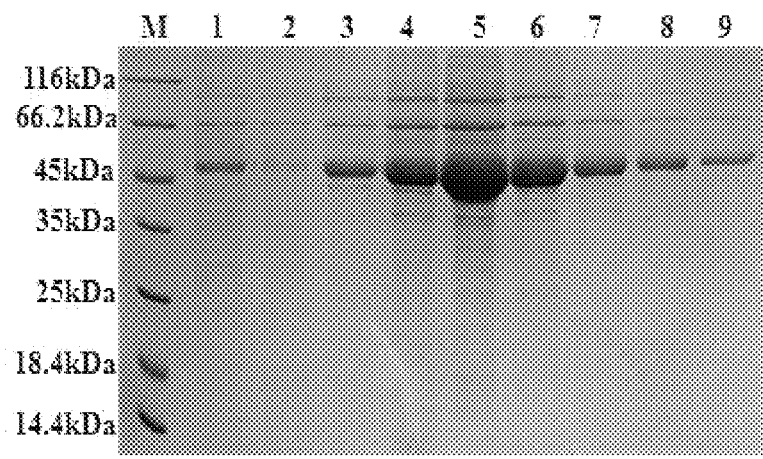
FIG. 1 shows the purification results of IL1β-hFc, wherein, M: protein molecular weight standard, 1: before injection of purification column, 2: flow through from purification column, and 3-9: eluates from purification column. The theoretical size of IL1β-hFc protein is 43.7 kDa, and the molecular weight of the protein dimer is about 87 kDa.
Figure 2:
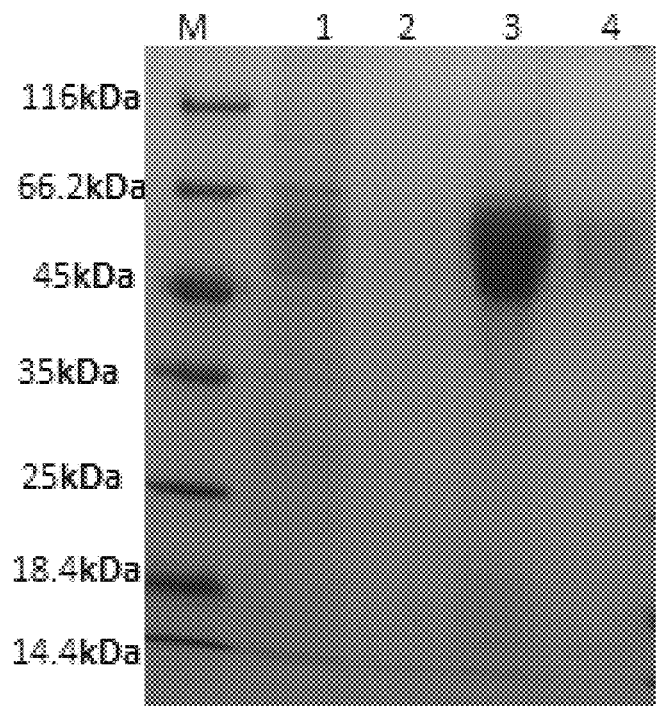
FIG. 2 shows the purification results of IL1RI (1-332)-HIS culture supernatant. M: protein molecular weight standard, 1: before injection of purification column, 2: flow through from purification column, and 3-4: eluates from purification column.

The experimental results are shown in FIGS. 1 and 2. FIG. 1 shows the results of purification of IL1β-hFc (IL1b-TEV-hIgG1Fc), IL1β-hFc protein was enriched and purified with a Protein A column (HiTrap Protein A HP, GE) and eluted, and the obtained protein was partially aggregated. The eluted samples were recovered, concentrated, exchanged, and stored at −80° C. FIG. 2 shows the results of purification of IL1RI (1-332)-HIS culture supernatant. IL1RI (1-332)-HIS protein was purified with a Ni Sepharose excel column (GE HealthcareLife Sciences) and eluted. The eluted samples were recovered, concentrated, exchanged and stored at −80° C.

1.2 Preparation of IL10-his (1) The amino acid sequence of human 1L1-beta (NCBI Reference Sequence: NP_000567.1) and His X6 tag were subjected to fusion design as follows (IL1b-His):

```
Amino acid sequence:
                                         (SEQ ID NO: 25)
MAPVRSLNCTLRDSQQKSLVMSGPYELKALHLuuoQGQDMEQQVVFSMSF

VQGEESNDKIPVALGLKEKNLYLSCVLKDDKPTLQLESVDPKNYPKKKME

KRFVFNKIEINNKLEFESAQFPNWYISTSQAENMPVFLGGTKGGQDITDF

TMQFVSSHHHHHH
```

(2) The amino acid sequence corresponding to the above fusion protein was subjected to manual codon optimization, and the optimized DNA was synthesized by GenScript and cloned into a pUC57simple (provided by GenScript) vector to obtain pUC57simple-IL1b-His plasmid.

(3) After restriction endonuclease digestion (Nco I and Xho 1) of the above plasmid, the gene fragments were recovered by electrophoresis, and ligated into linearized pET28a vector (NcoI&XhoI) and recombinantly constructed to obtain a pET28a-IL1b-His plasmid.

(4) The plasmid constructed above was transformed into BL21 (DE3) competent to obtain the expressed strains. The clones were selected and identified correctly and then expanded for culture. When the OD value reached 0.8-1.0, IPTG (Amresco) was added with a final concentration of 1 mM to induce at 16 degrees for 20 h; centrifuged to harvest the bacteria. The bacteria were resuspended using buffer A (50 mM Tris-HCl, 300 mM NaCl, 10 mM Imidazole, 5 mM B-ME, 10% glycerol, pH 8.0 (endotoxin controlled) and then crushed by high pressure, centrifuged at high speed for 1 h, vacuum filtered through a 0.45 μm microporous filter membrane to obtain the supernatant, which was purified using a Ni affinity chromatography column HisTrap FF (protein purification liquid chromatography system/AKTA Purifier 10, GE) according to the operating method provided by the manufacturer, to obtain the purified IL1b-His fusion protein.

Figure 3:
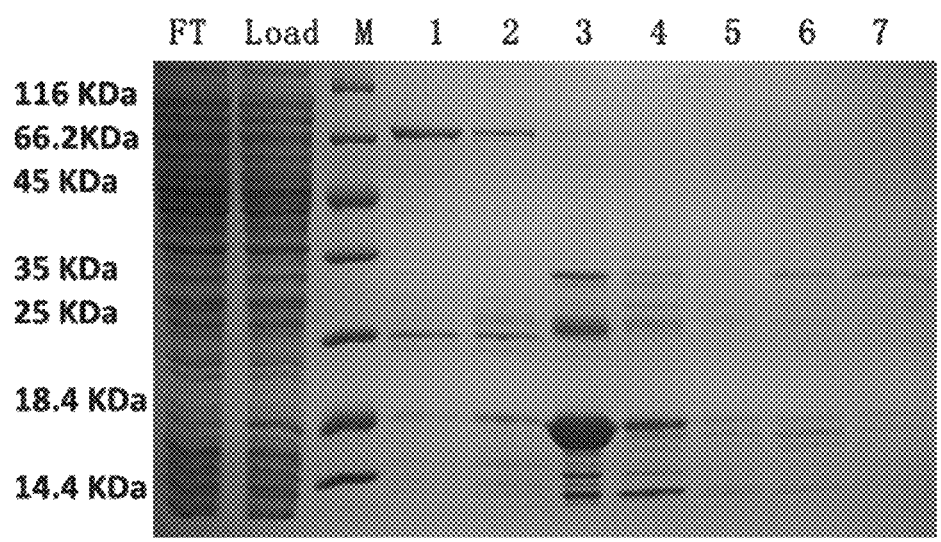
FIG. 3 shows the purification results of IL1b-His, M: protein molecular weight standard, FT: flow through from purification column, load; before injection of purification column, 1-7: eluates from purification column. The theoretical size of IL1b-His protein is 18.2 kDa, and there is no dimer molecule of the protein.

The experimental results of purification of IL1b-His are shown in FIG. 3. IL1b-His protein was enriched and purified with Ni affinity chromatography and eluted. The eluted samples were recovered, concentrated, exchanged and stored at −80° C. The subsequent QC test results showed that no aggregates appeared.

1.3 Preparation of IL1β-his-Bio and IL1RI-his-Bio (1) Preparation of the Protein to be Labeled IL-1β-His; molecular weight: 18572.14 g/mol, concentration. 1.068 mg/ml, volume: 1000 μL, total amount: 1068 μg. See Example 1.2 for the preparation method.

IL1RI (1-332)-His: molecular weight: 36859 g/mol, concentration: 1.22 mg/ml, volume: 1065 μL, total amount: 1.3 mg. See Example 1.1 for the preparation method.

(2) The commercially available biotin (molecular weight: 557 g/mol, Thermo) powder was placed at room temperature to equilibrate for about 15 min. 3 mg was weighed accurately, and dissolved in 540 μL of endotoxin-free water at a concentration of 5560 ng/ml, well-mixed for use.

(3) Calculation of the volume (μL) of biotin that needs to be added into the protein: Volume of biotin needed=(ng number of the protein to be labeled/molecular weight of the protein to be labeled)*20*557/5560 ng/ml.

(4) The corresponding volume of 5560 ng/ml of biotin solution was added to the solution of the two proteins to be labeled, and allowed to stand on ice for 1 hour, respectively.

(5) Through the HiTrap Desalting column (GE) in a protein purification instrument AKTA Purifier UPC 100 (GE), the solution was exchanged into PBS and the free biotin was removed. The protein was aliquoted, and quick-frozen in liquid nitrogen, and then stored at −80° C.

1.4 Preparation of Positive Control Antibody PcAb (1) According to the existing human IL1-beta (NCBI Reference Sequence: NP_000567.1) protein sequence and with reference to the anti-human IL1-beta antibody sequence according to U.S. Pat. No. 8,273,350 B2, the PcAb antibody has the following sequences:

```
Amino acid sequence of heavy chain variable
region of PcAb:
                                    (SEQ ID NO: 26)
QVQLVESGGGVVQPGRSLRLSCAASGFTFSVYGMNWVRQAPGKGLEWVAI

IWYDGDNQYYADSVKGRFTISRDNSKNTLYLQMNGLRAEDTAVYYCARDL

RTGPFDYWGQGTLVTVSS

Amino acid sequence of heavy chain constant
region of PcAb:
                                    (SEQ ID NO: 27)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Amino acid sequence of light chain variable
region of PcAb:
                                    (SEQ ID NO: 28)
EIVLTQSPDFQSVTPKEKVTITCRASQSIGSSLHWYQQKPDQSPKLLIKY

ASQSFSGVPSRFSGSGSGTDFTLTINSLEAEDAAAYYCHQSSSLPFTFGP

GTKVDIK

Amino acid sequence of light chain constant
region of PcAb:
                                    (SEQ ID NO: 29)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

(2) The amino acid sequences corresponding to the above antibody were subjected to manual codon optimization, and the optimized DNAs were synthesized by GenScript and cloned into a pUC57simple (provided by GenScript) vector to obtain pUC57simple-PCABH, pUC57simple-PCABL plasmids.

(3) After restriction endonuclease digestion (Xba I and BamH I) of the pUC57simple-PCABH, pUC57simple-PCABL plasmids, the gene fragments PCABH and PCABL were recovered by electrophoresis, and ligated with pcDNA3.1 vector and recombinantly constructed to obtain pcDNA3.1-PCABH, pcDNA3.1-PCABL.

(4) 7 days after the recombinant plasmids pcDNA3.1-PCABH and pcDNA3.1-PCABL constructed above were transfected into FreeStyle™ 293-F cells, the culture solution was centrifuged at high speed and vacuum filtered through a microporous filter membrane, and purified using a Protein A column (protein purification liquid chromatography system/AKTA Purifier 10, GE) according to the operating method provided by the manufacturer, to obtain the purified antibody PCAB.

Figure 4:
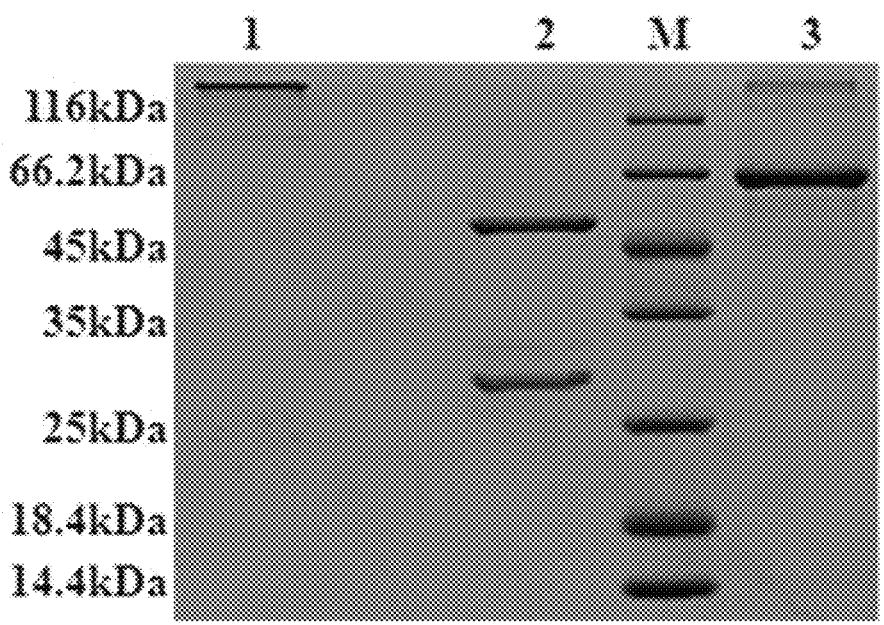
FIG. 4 shows the purification results of PcAb. M: protein molecular weight standard, 1: non-reduced antibody, 2: reduced antibody, 3: BSA control. The theoretical size of PcAb protein is 150 kDa, the heavy chain molecular weight of the antibody is about 45 kDa, and the light chain molecular weight is about 30 kDa.

The experimental results of the purification of PcAb are shown in FIG. 4. The PcAb protein was enriched and purified with a Protein A column and eluted. The eluted samples were recovered, concentrated, exchanged and stored at −80° C.

1.5 Preparation of Murine Antibody (1) The immunogen IL1β-his (see Example 1.2 for the preparation method) was emulsified with adjuvant at a volume ratio of 1:1. Freund's complete adjuvant (FCA, Sigma, F5881-10×10 ml) was used for the first immunization; the second immunization was performed after 2 weeks, the antigen was emulsified using Freund's incomplete adjuvant (FIA, Sigma. F5881-10×10 ml), and the mice were injected subcutaneously at 5 points, with 50 μg of antigen for each mouse (BALB/C mouse, SPF grade, female, 6 weeks old), and a volume of 50 μL at each injection point.

(2) 10 days after the second immunization, a small amount of blood sample was collected from the tail of each mouse for serum titer testing. When the serum titer reached 1:81000 or above by indirect ELISA, the mice were boost immunized.
(3) The mice that had been boost immunized were sacrificed and dissected. The spleens were separated and ground to prepare a single cell suspension through cell strainers, which was mixed with myeloma cells SP2/0-14Ag at a ratio of 5:1, centrifuged and dispersed the cell mass, and then slowly dropwise added with PEG/DMSO SOLUTION (Sigma) in a 37° C. water bath to complete the cell fusion. After centrifugation (1500 rpm), the cells were resuspended in IMDM medium (Hyclone) containing 1×HAT (50×, Sigma), 15% fetal bovine serum (Gibco), 1×Penicillin-Streptomycin and plated into 96-well cell culture plates for culture.
(4) The 96-well cell culture plates were screened by indirect ELISA. The positive clones obtained by primary screening were subjected to the second round of three-point dilution screening by indirect ELISA, followed by the third round of screening with the stock solution by competitive ELISA, and finally the target positive clones were obtained.
(5) The target positive clones obtained by above screening were subjected to two rounds of subcloning by limited dilution method, each round of subcloning was screened by indirect ELISA, and finally the stable cell line was obtained.
(6) The obtained stable cell line was cultured in IMDM medium containing low IgG fetal bovine serum, and finally the cell culture supernatant was purified to obtain a monoclonal antibody.

Example 2 Test of Murine Antibody 2.1 Determination of Binding Affinity of Murine Antibodies to Antigen IL1β(ELISA)

(1) Streptavidin (1.0 mg/ml, Sangon) was diluted to 2 μg/ml with CBS (0.05 M carbonate coating buffer) and used for coating ELISA plate at 50 μL/well, incubated overnight at 4° C., washed the plate once with PBST.
(2) 0.2 μg/ml IL-1β-his-bio was added into ELISA plate (see Example 1.3 for the preparation method), 50 μL/well, incubated 30 min at 37° C., washed the plate 3 times with PBST (plate washing liquid).
(3) 1% BSA in PBS was added (1 g of BSA dry powder, added with PBS to make up to 100 ml of solution) for blocking, 300 μL/well, incubated 30 min at 37° C., washed the plate 3 times with PBST.
(4) The antibodies (see Example 1.5 for the preparation method of the murine antibody, and Example 1.4 for the preparation method of the control antibody PcAb) were diluted to 1 μg/ml, and further diluted 3-fold down for a total of 7 concentration gradients, using the diluent as a zero-point control: 50 μL/well, incubated 30 min at 37° C.: washed the plate 3 times with PBST. The information of the 5 murine antibodies is as follows:

| Antibody name | Concentration (μg/ml) |
|---|---|
| KF021ZP4 9D5 | 2.17 |
| KF021ZP4 18B1 | 1.56 |
| KF021ZP4 18E1 | 1.5 |
| KF021ZP4 18H11 | 0.4 |
| KF021ZP4 19E4 | 0.14 |

(5) The secondary antibody HRP conjugated Goat Anti Mouse IgG (1:5000) (preparation of the enzyme-labeled secondary antibody solution: 1 μL of Goat Anti Mouse IgG(H+L), HRP secondary antibody mother liquor was taken using a pipette and mixed well with 5 ml of 1% BSA buffer under shaking. That is, the secondary antibody was diluted at a ratio of 1:5000, prepared freshly.) and HRP conjugated Goat Anti Human IgG (15000) (preparation of the enzyme-labeled secondary antibody solution: 1 μL of Goat Anti Human IgG, HRP secondary antibody mother liquor was taken using a pipette and mixed well with 5 ml of 1% BSA buffer under shaking. That is, the secondary antibody was diluted at a ratio of 1:5000, prepared freshly.) were added into the plate, 50 μL/well, incubated 30 min at 37° C., washed the plate 4 times with PBST
(6) 50 μL TMB (Neogen) was added into each well for color development. After reacting in the dark at room temperature for 5 min, a stop solution was added to stop the reaction. The absorbance was read at 450 nm.

Figure 5:
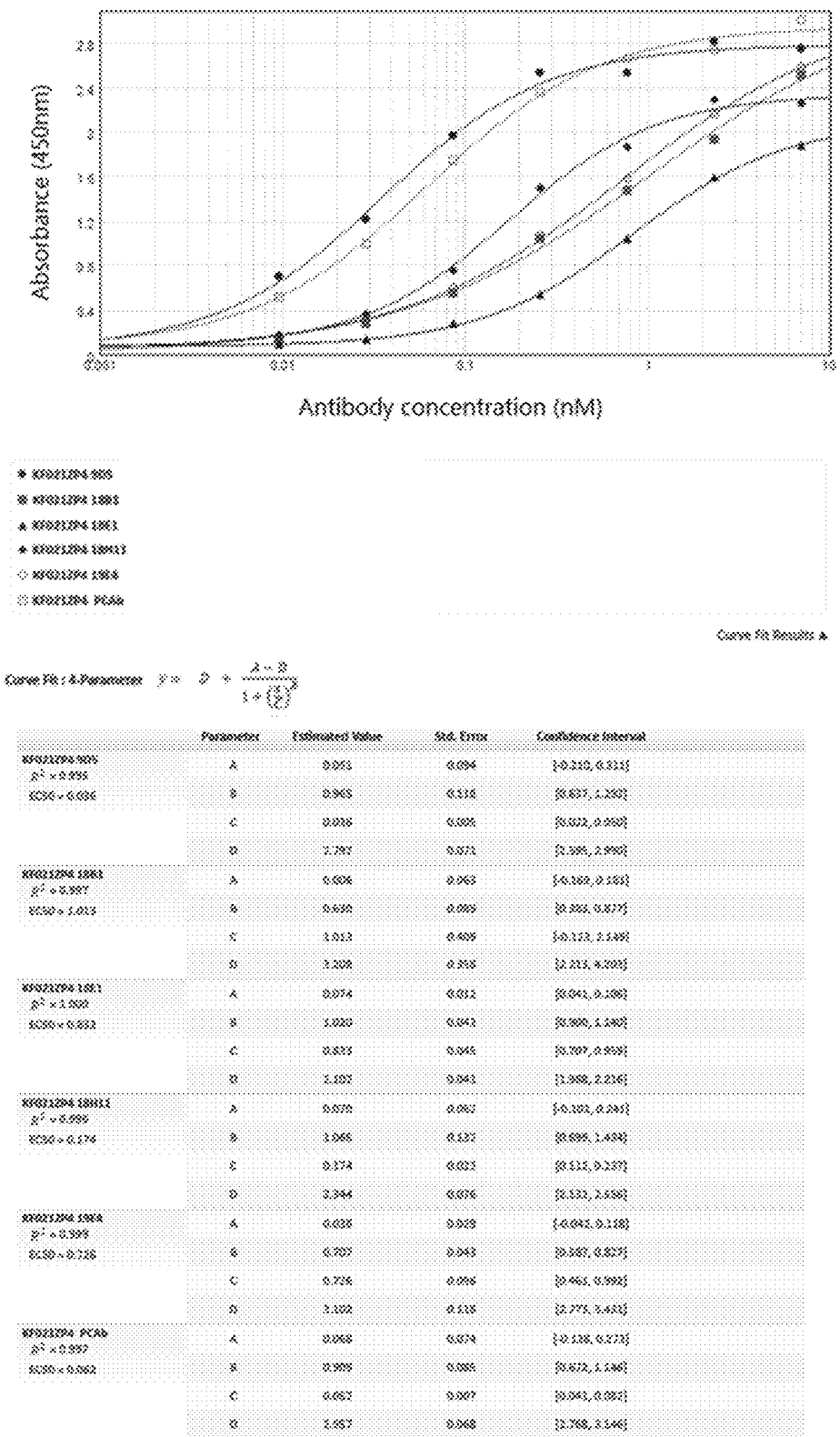
FIG. 5 shows the ELISA results of the binding affinity of the murine antibodies to antigen IL1β.

The experimental results are shown in Table 1 and FIG. 5. The results indicate that: KF021ZP4 9D5, KF021ZP4 18B1, KF021ZP4 18E1, KF021ZP4 18H11, KF021ZP4 19E4 all bind to IL-1β-his-bio.

TABLE 1

The binding affinity results of murine antibodies to antigen IL1β

| Antibody name | $EC_{50}$ (nM) of binding |
|---|---|
| KF021ZP4 9D5 | 0.036 |
| KF021ZP4 18B1 | 1.013 |
| KF021ZP4 18E1 | 0.833 |
| KF021ZP4 18H11 | 0.174 |
| KF021ZP4 19E4 | 0.726 |
| KF021ZP4 PcAb | 0.062 |

2.2 Determination the Affinity of Murine Antibodies Competing with IL1RI for Binding to Antigen IL1β(ELISA)

(1) IL-1β-hFc (see Example 1.1 for the preparation method) was diluted to 4 μg/ml and coating ELISA plate, 50 μL/well, and incubated overnight at 4° C., washed the plate once with PBST.
(2) 1% BSA in PBS was added into the plate for blocking, 300 μL/well, incubated 30 min at 37° C., washed the plate 3 times with PBST.
(3) The antibodies (same as Example 2.1) were diluted to 2 μg/ml (final concentration 1 μg/ml), and further diluted 3-fold down for a total of 7 concentration gradients, using the diluent as a zero-point control; 50 μL/well, incubated at room temperature for 10 min; added 0.08 μg/ml of IL1RI(1-332)-his (final concentration 0.04 μg/ml, see Example 1.1 for the preparation method), 50 μL/well, mixed well and incubated at 37° C. for 30 min, washed the plate 3 times with PBST.

(4) The secondary antibody Mouse anti His, HRP conjugated (1:8000) was added into the plate, 50 μL/well, incubated 30 min at 37° C., washed the plate 4 times with PBST.

(5) 50 μL TMB was added into each well for color development. After reacting in the dark at room temperature for 5 min, a stop solution was added to stop the reaction. The absorbance was read at 450 nm.

Figure 6:
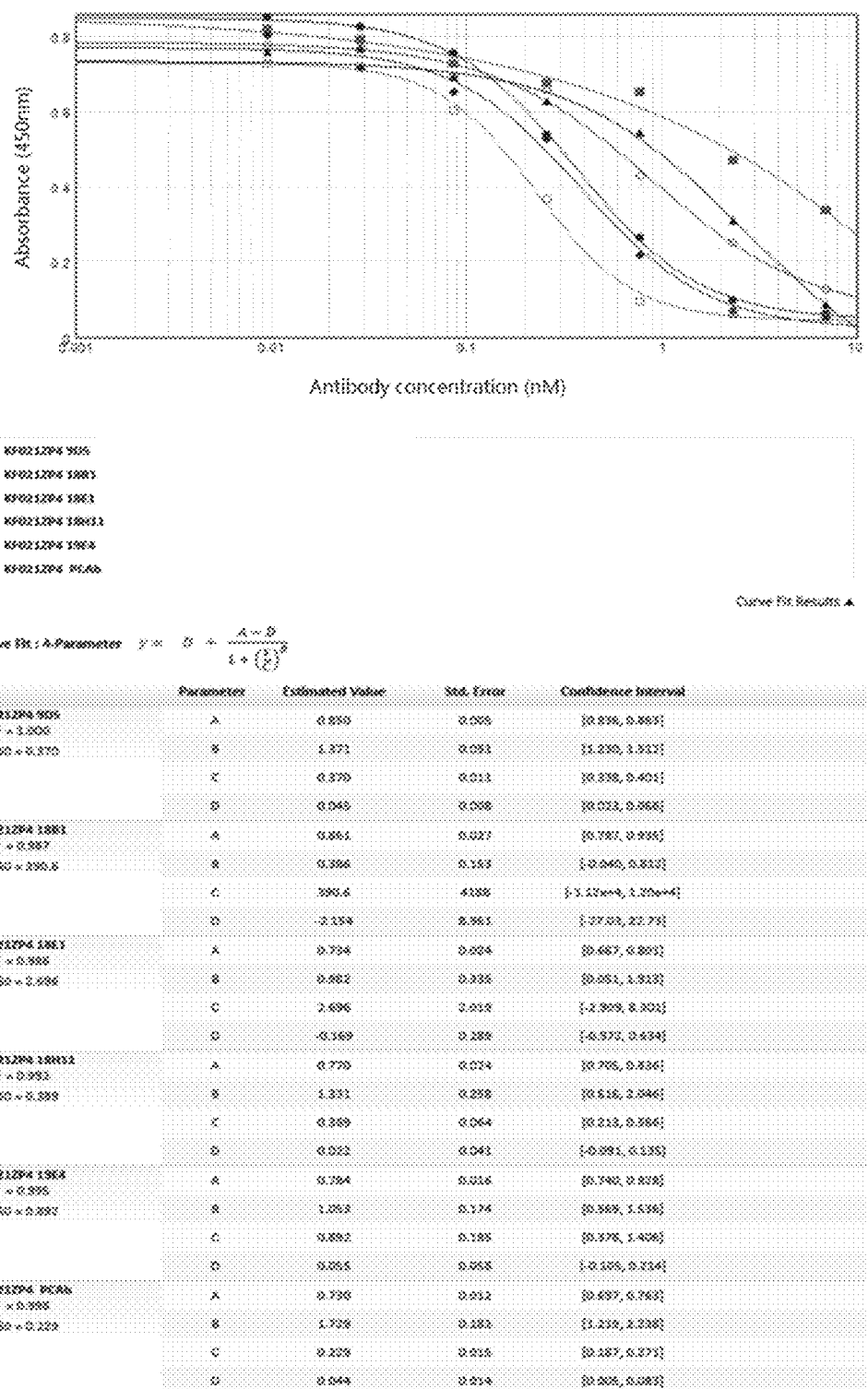
FIG. 6 shows the ELISA results of the affinity of the murine antibodies competing with IL1RI for binding to antigen IL1β.

The experimental results are shown in Table 2 and FIG. 6. The results indicate that: KF021ZP4 9D5, KF021ZP4 18B1, KF021ZP4 18E1, KF021ZP4 18H11, KF021ZP4 19E4 can effectively block the binding of IL-1β-hFc to IL1RI (1-332)-his.

TABLE 2

The affinity of murine antibodies competing with IL1R1 for binding to antigen IL1β

| Antibody name | $EC_{50}$ (nM) of binding |
| --- | --- |
| KF021ZP4 9D5 | 0.37 |
| KF021ZP4 18B1 | 390.6 |
| KF021ZP4 18E1 | 2.696 |
| KF021ZP4 18H11 | 0.389 |
| KF021ZP4 19E4 | 0.892 |
| KF021ZP4 PCAb | 0.229 |

2.3 Detection of Inhibition of Murine Antibodies on IL1β-Induced IL6 Secretion in Cells (1) The well-growing MRC-5 cells (Cell Center of the Chinese Academy of Sciences) were digested with trypsin (Gibco), counted, inoculated into a 96-well cell culture plate, and grown overnight.

(2) The negative control group (MRC-5 cells+IL-1β+mIgG or MRC-5 cells+IL-1β+hIgG), the positive control group (MRC-5 cells+IL-1β+PcAb) and the test group (MRC-5 cells+IL-1β +different concentrations of antibodies) were designed according to the requirements, the cells were cultured in a cell incubator at 37° C. for 24 hours.

Wherein:

IL-1β(Sino, concentration 588 nM);

Positive antibody PcAb (see Example 1.4 for the preparation method, concentration 3.4 mg/mL);

Antibody 9D5 (see Example 1.5 for the preparation method, concentration 2.17 mg/mL);

Antibody 18E1 (see Example 1.5 for the preparation method, concentration 1.8 mg/mL);

Antibody 18B1 (see Example 1.5 for the preparation method, concentration 1.56 mg/mL);

Antibody 18H11 (see Example 1.5 for the preparation method, concentration 0.4 mg/mL);

Antibody 19E4 (see Example 1.5 for the preparation method, concentration 0.14 mg/mL);

(3) After 24 hours, the cell supernatant was taken for IL-6 detection. Quantitative detection was performed with an ELISA kit (Daktronics), and the specific operation was carried out in accordance with the kit instructions.

Figure 7:
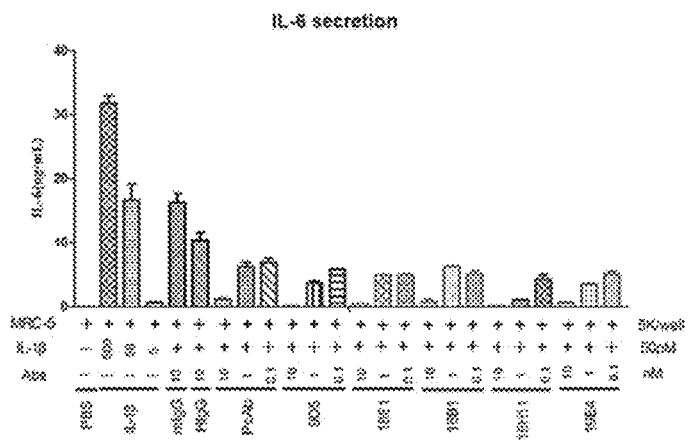
FIG. 7 shows the ELISA results of inhibition of the murine antibodies on IL1β-induced IL-6 secretion in MRC5 cells.

The detection results of IL-6 are shown in FIG. 7. Experimental results indicate that IL-1β can induce MRC-5 cells to secrete IL-6, and the antibodies 9D5, 18E1, 18B1, 18H11 and 19E4 can effectively block the process of IL-1β stimulating MRC-5 cells to secrete IL-6. Among them, 9D5, 18H11 and 19E4 are more effective in blocking IL-1β-induced IL-6 secretion.

The three murine antibodies of 9D5, 18H11 and 19E4 with better affinities were selected for in vivo pharmacological study.

Example 3 In Vivo Pharmacological Study of Murine Antibodies

Main materials

1) Experimental animals

Balb/c mice: SPF grade, female, 4-6 weeks old, 29 mice, source: Beijing Charles River Laboratories Co., Ltd., animal quality certificate: 11400700113776.

Balb/c mice: SPF grade, female, 6-8 weeks old, 18 mice, source: Guangdong Medical Experimental Animal Center, animal quality certificate: 44007200023548.

2) Cells

NIH/3T3 (ATCC, Cell passage: 15th passage)

Lenti-IL-1β-NIH/3T3 (transfected in our laboratory, Cell passage: 11 th passage)

3) Antibodies

Negative control: Anti-HEL (Akesobio)

Positive control: PcAb

Candidate antibodies: 9D5, 18H11, 19E4

Sodium chloride injection (Zhejiang Tianrui Pharmaceutical Co., Ltd.)

Experimental procedures:

1) Drug preparation

Antibody Anti-HEL 2 mg/ml (for model group): 0.984 ml (4.8 mg) of stock solution (concentration: 4.88 mg/ml) was added to 1.416 ml of sodium chloride injection, a total of 2.4 ml. Antibody PcAb 2 mg/ml (for positive drug group): 0.627 ml (4.8 mg) of stock solution (concentration: 7.65 mg/ml) was added to 1.773 ml of sodium chloride injection, a total of 2.4 ml. Antibody 9D5 2 mg/ml (for 9D5 group): 0.842 ml (4.8 mg) of stock solution (concentration: 5.70 mg/ml) was added to 1.558 ml of sodium chloride injection, a total of 2.4 ml. Antibody 18H11 2 mg/ml (for 18H11 group): 1.450 ml (4.8 mg) of stock solution (concentration: 3.31 mg/ml) was added to 0.950 ml of sodium chloride injection, a total of 2.4 ml. Antibody 19E4 2 mg/ml (for 19E4 group): 0.767 ml (4.8 mg) of stock solution (concentration: 6.26 mg/ml) was added to 1.633 ml of sodium chloride injection, a total of 2.4 ml.

2) Animal grouping 47 mice were randomly divided into 5 groups according to the body weight: normal group (sodium chloride injection, 10 ml/kg, n=7), model group (Anti-HEL, 20 mg/kg, n=8), positive drug group (PcAb, 20 mg/kg, n=8), 19E4 group (19E4, 20 mg/kg, n=8), 18H1 group (18H11, 20 mg/kg, n=8), 9D5 group (9D5, 20 mg/kg), N=8), respectively.

3) Administration: by tail vein injection.

4) Cell inoculation

Balb/c mice were anesthetized by intraperitoneal injection of chloral hydrate, and then inoculated with the corresponding cell suspension into the left knee joints of mice, wherein: the normal group was inoculated with NIH/3T3 (inoculated with 50,000 cells/mouse), and the other groups (model group, positive drug group, 19E4 group, 18H11 group and 9D5 group) were inoculated with Lenti-IL-1β-NIH/3T3 (inoculated with 50,000 cells/mouse).

5) Weight measurement: The body weight of the mice was measured on the 3rd and 5th day after inoculation.

6) Behavior scoring and knee joint measurement

On the 5th day after inoculation, the mice were scored behaviorally, meanwhile, the mice were euthanized and dissected, the length and width of the knee joint albuginea were measured with a vernier caliper.

Behavioral scoring criteria:

Score 0: the mouse has normal activity and can move bilaterally.

Score 1: the mouse walks abnormally and can move bilaterally.

Score 2: the affected limb of the mouse touches the ground briefly and can move bilaterally.

Score 3: the affected limb of the mouse cannot touch the ground and moves unilaterally.

Experimental Results

1) Effect of the Antibodies 19E4, 18H11 and 9D5 on the Behavior of Mice

Figure 8:
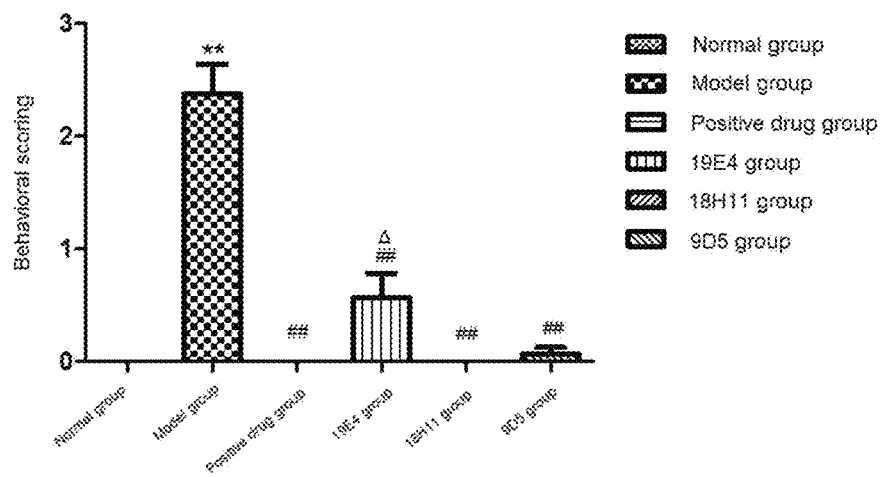
FIG. 8 shows the effects of the murine antibodies 19E4, 18H1 and 9D5 on the behavior of mice. Compared with the normal group, **$P<0.01$; compared with the model group, ##$P<0.01$; compared with the positive drug group, $^{\Delta}P<0.01$; n=8 (normal group n=7).

The experimental results are shown in FIG. 8. Compared to the normal group, the mice in the model group had obvious behavioral abnormalities (P<0.01). After administration, compared to the model group, the positive drug can significantly reduce behavioral abnormalities in mice (P<0.01), and the three candidate antibodies (19E4, 18H11, 9D5) also significantly reduced behavioral abnormalities in mice (P<0.01). Compared to the positive drug group, the efficacy of 19E4 in reducing behavioral abnormalities in mice was inferior to that of the positive drug group (P<0.05), and the efficacy of 18H11 and 9D5 in reducing behavioral abnormalities in mice was equivalent to that of the positive drug (P>0.05); 18H11 and 9D5 had an equivalent efficacy in reducing behavioral abnormalities in mice (P>0.05).

2) Effect of the Antibodies 19E4, 18H11 and 9D5 on Knee Joint Swelling in Mice

Figure 9:
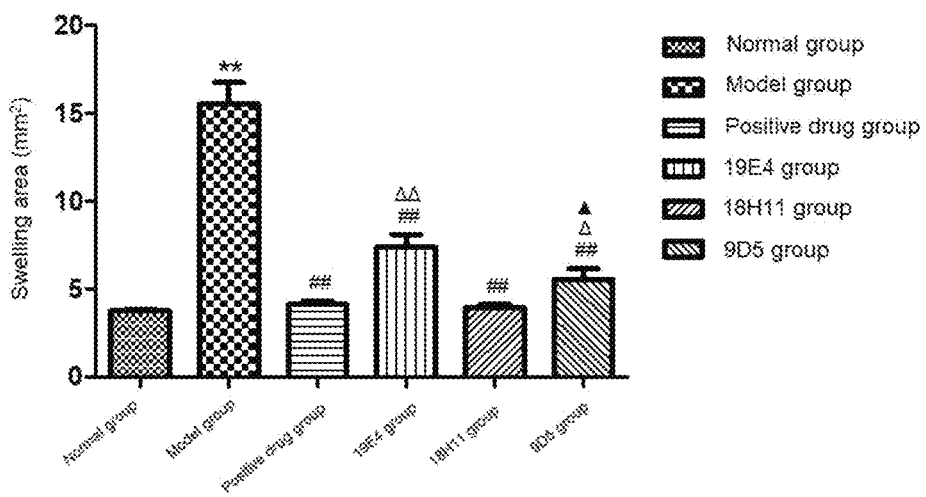
FIG. 9 shows the effects of the murine antibodies 19E4, 18H11 and 9D5 on knee joint swelling n mice. Compared with the normal group, **$P<0.01$; compared with the model group, ##$P<0.01$; compared with the positive drug group, $^{\Delta}P<0.01$: compared with the 18H11 group, $^{\Delta}P<0.05$; n=8 (normal group n=7).

The experimental results are shown in FIG. 9. The area of knee joint swelling caused in the model group was significantly higher than that in the normal group (P<0.01). After administration, the positive drug significantly reduced the knee joint swelling area in mice (P<0.01), and the 3 candidate antibodies (19E4, 18H11, 9D5) also significantly reduced the knee joint swelling area in mice (P<0.01). Compared to the positive drug, the efficacy of 19E4 in reducing the knee joint swelling area in mice was inferior to that of the positive drug (P<0.01), the efficacy of 18H11 in reducing the knee joint swelling area in mice was equivalent to that of the positive drug (P>0.05), and the efficacy of 9D5 in reducing the knee joint swelling area in mice was weaker than that of the positive drug (P<0.05). Compared to 9D5, 18H11 had better efficacy in reducing the knee joint swelling area in mice (P<0.05).

3) Effect of the Antibodies 19E4, 18H11 and 9D5 on the Body Weight of Mice

The experimental results are shown in Table 3. The body weight of mice in the model group was significantly lower than that in the normal group (P<0.01). The positive drug had no obvious effect on the body weight of mice, (P<0.01); 19E4 reduced the body weight of mice slightly weaker than the model group; 18H11 and 9D5 had no significant effect on the body weight of mice, which was equivalent to that of the positive drug (P>0.05); 18H11 and 9D5 had an equivalent effect on the body weight of mice (P>0.05).

TABLE 3

Effect of 19E4, 18H11 and 9D5 on the body weight of mice (±SD, n = 8)

| Group | Body weight (g) | | |
|---|---|---|---|
| | Day 0 | Day 3 | Day 5 |
| Normal group | 19.3 ± 1.72 | 20.3 ± 1.68 | 20.0 ± 1.71 |
| Model group | 19.3 ± 1.39 | 17.9 ± 1.63* | 17.4 ± 1.51** |
| Positive drug group | 19.3 ± 1.08 | 19.2 ± 1.36 | 19.7 ± 1.18## |
| 19E4 group | 19.4 ± 0.98 | 18.4 ± 1.02 | 18.6 ± 1.13##ΔΔ |
| 18H11 group | 19.4 ± 1.04 | 19.5 ± 0.88# | 19.7 ± 0.60## |
| 9D5 group | 19.4 ± 1.04 | 19.1 ± 0.85 | 19.5 ± 0.92## |

Compared to the normal group, **P < 0.01, *P < 0.05;
Compared to the model group, ##P < 0.01, #P < 0.05;
Compared to the positive group, ΔΔP < 0.01;
n = 8 (normal group n = 7).

The results of this experiment indicate that the candidate antibodies 19E4, 18H11, and 9D5 can significantly reduce IL-1β-induced arthritis lesions in mice, and the efficacy of the candidate antibodies 18H11 and 9D5 is equivalent to that of the positive control antibody PcAb. Based on the experimental data of behavior scoring and knee joint swelling in mice, 18H11 is better than 9D5 under the experimental conditions.

By sequencing, the candidate antibodies 18H11, 19E4, and 9D5 have the sequence information as follows:

18H11 comprises a heavy chain variable region having the amino acid sequence as shown in SEQ ID NO: 7, and the nucleotide sequence as shown in SEQ ID NO: 15; and a light chain variable region having the amino acid sequence as shown in SEQ ID NO: 8, and the nucleotide sequence as shown in SEQ ID NO:16.

19E4 comprises a heavy chain variable region having the amino acid sequence as shown in SEQ ID NO: 30, and the nucleotide sequence as shown in SEQ ID NO: 31; and a light chain variable region having the amino acid sequence as shown in SEQ ID NO: 32, and the nucleotide sequence as shown in SEQ ID NO: 33.

9D5 comprises a heavy chain variable region having the amino acid sequence as shown in SEQ ID NO: 34, and the nucleotide sequence as shown in SEQ ID NO: 35; and a light chain variable region having the amino acid sequence as shown in SEQ ID NO: 36, and the nucleotide sequence as shown in SEQ ID NO: 37.

Example 4 Preparation of Recombinant Antibody and Determination the Affinity 4.1 Preparation of the Recombinant Antibodies 18H11 (RE), 19E4 (RE), 9D5 (RE)

The heavy chain cDNA sequences (the heavy chain variable region sequences are shown in SEQ ID NO: 15, SEQ ID NO: 31, SEQ ID NO: 35; the constant region sequence is immunoglobulin gamma 2b heavy chain precursor [Mus musculus] 140-475. ACCESSION: ACX70084.1) and light chain cDNA sequences (the light chain variable region sequences are shown in SEQ ID NO: 16, SEQ ID NO: 33, SEQ ID NO: 37; the constant region is antibody kappa light chain, partial [Mus musculus], 106-213 GenBank: BAB33404.1) of 18H11, 19E4, and 9D5 were cloned into a pUC57simple vector (provided by GenScript) to obtain the pUC57simple-18H11H/19E4H/9D5.12H and pUC57simple-18H11L/19E4L/9D5.12L plasmids.

The pUC57simple-18H11H/19E4H/9D5.12H and pUC57simple-18H11 L/19E44J9D5.12L plasmids were restriction endonuclease digested (HindiII&EcoRI), and the obtained heavy and light chains recovered by electrophoresis were subcloned into a pcDNA3.1 vector, respectively, and the recombinant plasmids were extracted and co-transfected into 293F cells. After culturing the cells for 7 days, the culture solution was centrifuged at high speed and vacuum filtered through a microporous membrane, and then loaded onto a HiTrap MabSelectSuRe column. The proteins were eluted in one step with Elution Buffer, and the target samples were recovered and exchanged into PBS using HiTrap Desalting.

4.2 Affinity Test of Recombinant Antibody

The binding affinity of the recombinant antibodies 18H11 (RE), 19E4 (RE), and 9D5 (RE) to antigen IL1β (ELISA), and the affinity of the recombinant antibodies competing with IL1RI for binding to antigen IL1β were carried out referring to the methods in Examples 2.1 and 2.2.

The test results indicate that: the recombinant antibodies 18H11 (Re), 19E4 (Re) and 9D5 (Re) all bind to 1L1β, and have an equivalent binding activity to that of the murine antibodies 18H11, 19E4 and 9D5 and the positive control antibody PCAb; the recombinant antibodies 18H11 (Re), 19E4 (Re) and 9D5 (Re) can effectively block the binding of IL1(i to IL1RI, among them, the affinity of 18H11(Re) competing with IL1RI for binding to antigen IL1β is equivalent to that of the murine antibody 18H11 and the positive control antibody PCAb.

Example 5 Construction of Humanized Antibody

In the present invention, based on the sequence of the murine antibody 18H11, the heavy chain and light chain variable regions were divided into 14 structurally meaningful peptide segments, and compared to the corresponding antibody segments of known structures in the PDB database. The corresponding segment with the highest sequence homology was selected from multiple sequence alignments to simulate the structure of this segment. Then all the simulated structural segments were combined to construct the variable region structure. A reliable antibody structure model was obtained by performing multiple rounds of energy minimization on the model.

While building the structural model, the mouse VH and VL amino acid sequences were compared to the human germline sequences in the database, to select a sequence with the highest homology. Through very careful examination of each of the different amino acids in the above-obtained three-dimensional structure model, it was determined whether it has a potential impact on structural integrity and CDR regions. Identical amino acids in the human sequence were also taken into account to ensure maximum humanization of the sequence. Before determining the final sequence, the potential glycosylation sites were also searched and removed without affecting the binding capacity of the antibody. The final humanized genes were named 18H11 H1, 18H11 H2, 18H11 L1, 18H11 L2, etc. (antibody constant region sequence, from NCBI database, heavy chain constant region: Ig gamma-1 chain C region, ACCESSION: P01857, light chain constant region: Ig kappa chain C region, ACCESSION; P01834).

The humanized antibody 18H11H1L1 comprises a heavy chain variable region having the amino acid sequence as shown in SEQ ID NO: 9, and the nucleotide sequence as shown in SEQ ID NO: 17: and a light chain variable region having the amino acid sequence as shown in SEQ ID NO: 10, and the nucleotide sequence as shown in SEQ ID NO: 18.

The humanized antibody 18H11H2L2 comprises a heavy chain variable region having the amino acid sequence as shown in SEQ ID NO: 11, and the nucleotide sequence as shown in SEQ ID NO: 19; and a light chain variable region having the amino acid sequence as shown in SEQ ID NO: 12, and the nucleotide sequence as shown in SEQ ID NO: 20.

The humanized antibody 18H11H3L3 comprises a heavy chain variable region having the amino acid sequence as shown in SEQ ID NO: 13, and the nucleotide sequence as shown in SEQ ID NO: 21: and a light chain variable region having the amino acid sequence as shown in SEQ ID NO: 14, and the nucleotide sequence as shown in SEQ ID NO: 22.

Wherein, the heavy chain complementarity determining region has the amino acid sequences of HCDR1: GYLFTGYY (SEQ ID NO: 1), HCDR2: ISCYNGDT (SEQ ID NO: 2) and HCDR3: SRSDYYGTSDY (SEQ ID NO: 3), and the light chain complementarity determining region has the amino acid sequences of LCDR1: SSVSY (SEQ ID NO: 4), LCDR2: TTS (SEQ ID NO: 5) and LCDR3: QQRIIYPPT (SEQ ID NO: 6).

Example 6 Test of Humanized Antibody 6.1 the Binding Affinity Determination of Humanized Antibody to Antigen IL1P (ELISA)

IL-1β-his was diluted and coated on ELSIA plate with CBS, incubated overnight at 4° C., washed once with PBST. 1% BSA in PBS was added for blocking at 37° C. for 30 min, washed 3 times with PBST. The antibody (Table 4) was diluted gradually and added into the plate, incubated at 37° C. for 30 min, washed 3 times with PBST. The secondary antibody HRP conjugated Goat Anti Human IgG (1:5000) was added into the plate (preparation of the enzyme-labeled secondary antibody solution: 1 μL of Goat Anti Human IgG, HRP secondary antibody mother liquor was taken using a pipette and mixed well with 5 ml of 1% BSA buffer under shaking. That is, the secondary antibody was diluted at a ratio of 1:5000, prepared freshly.), incubated at 37° C. for 30 min, washed 4 times with PBST. 50 μL of TMB was added to each well for color development. After reacting in the dark at room temperature for 5 min, a stop solution was added to stop the reaction. The absorbance was read at 450 nm.

TABLE 4

Information of three humanized antibodies

| Antibody name | Concentration (mg/ml) |
| --- | --- |
| KF021ZP4 18H11 H1L1 | 5.0 |
| KF021 ZP4 18H11 H2L2 | 1.5 |
| KF021 ZP4 18H11 H3L3 | 5.24 |

Figure 10:
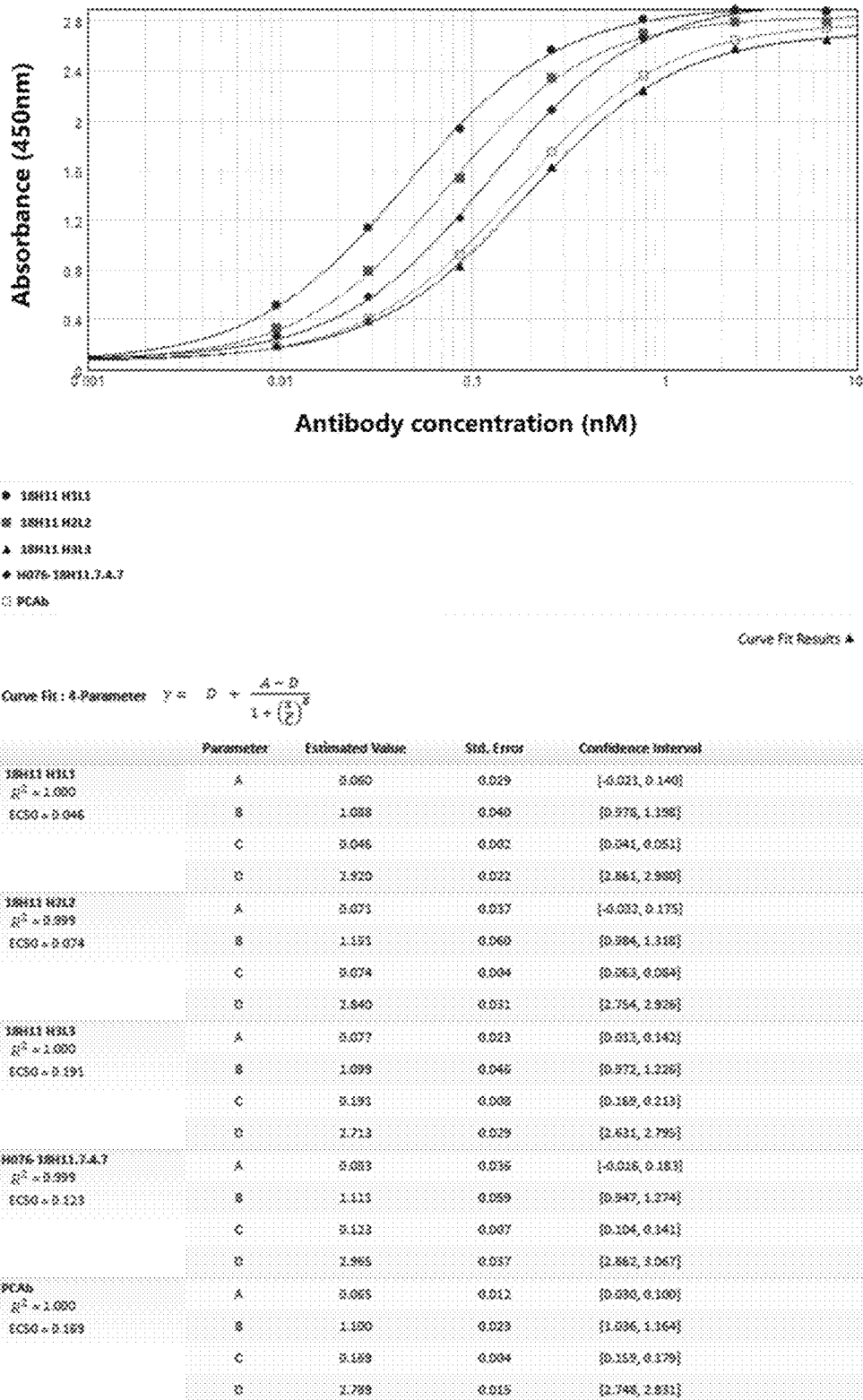
FIG. 10 shows the ELISA results of the binding affinity of the humanized antibodies to antigen IL1β.

The experimental results are shown in Table 5 and FIG. 10. The results indicate that: 18H11H1L1, 18H Ill H2L2, 18H11H3L3 all can bind to IL-1β-his.

TABLE 5

The binding affinity results of humanized antibodies to antigen IL1β

| Antibody name | $EC_{50}$ (nM) of binding |
|---|---|
| 18H11 H1L1 | 0.046 |
| 18H11 H2L2 | 0.074 |
| 18H11 H3L3 | 0.191 |
| KF021ZP4 PCAb | 0.169 |

6.2 Affinity Test of Humanized Antibodies Competing with IL1RI for Binding to Antigen IL1β (ELISA)

IL-1β-hFc was diluted and coated on ELISA plate with CBS, and incubated overnight at 4° C., washed once with PBST. 1% BSA in PBS was added into the plate for blocking at 37° C. for 30 min, washed 3 times with PBST. The antibodies (Table 4) in gradient dilution were added into the plate and incubated at room temperature for 10 min. IL1RI (1-332)-his was added, mixed well with the antibody, and then incubated at 37° C. for 30 min, and then washed 3 times with PBST. Mouse anti His, HRP conjugated (cwbio) was added, 37° C. for 30 min, washed 4 times with PBST. 50 μL of TMB was added to each well for color development. After reacting in the dark at room temperature for 5 min, a stop solution was added to stop the reaction. The absorbance was read at 450 nm.

Figure 11:
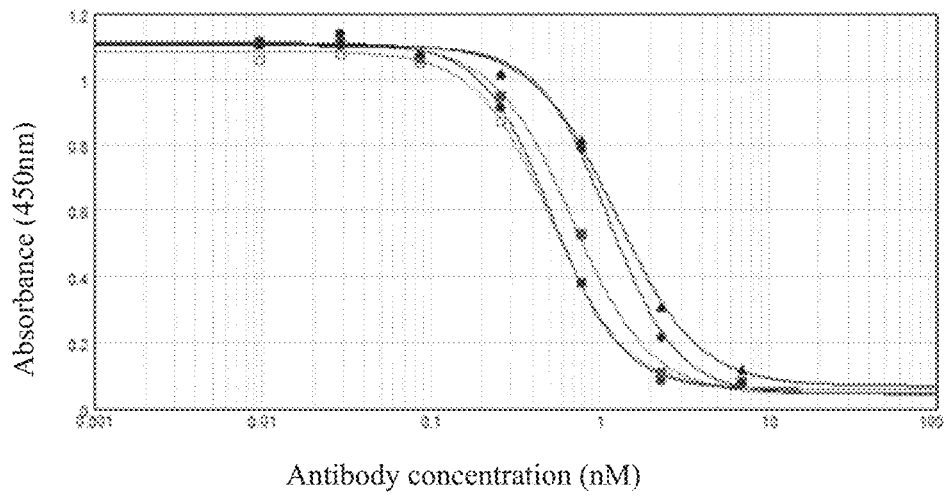
FIG. 11 shows the ELISA results of the affinity of the humanized antibodies competing with IL1RI for binding to antigen IL1β.

The experimental results are shown in Table 6 and FIG. 11. The results indicate that: 18H11H1L1, 18H11H2L2, 18H11H3L3 can effectively block the binding of IL-1β-hFc to IL1RI (1-332)-his.

TABLE 6

The affinity of humanized antibodies competing with IL1R1 for binding to antigen IL1β

| Antibody name | $EC_{50}$ (nM) of binding |
|---|---|
| 18H11 H1L1 | 0.520 |
| 18H11 H2L2 | 0.683 |
| 18H11 H3L3 | 1.251 |
| KF021ZP4 PCAb | 0.516 |

6.3 Detection of Inhibition of Humanized Antibodies on IL1β-Induced IL6 Secretion in Cells (1) The well-growing MRC-5 cells (Cell Center. Chinese Academy of Sciences) were digested with trypsin (Gibco), counted, inoculated into a 96-well cell culture plate, and grown overnight.

(2) IL-1β and PcAb or the antibodies to be tested were incubated at 37° C. for 20 min, and added to the cells for 24 hours. Wherein:

IL-1β (Sino, concentration 588 nM):
Positive antibody PcAb (concentration 3.4 mg/mL);
Control antibody hIgG (concentration 4.88 mg/mL)
Antibody to be tested 18H11H1L1 (concentration 5 mg/mL)
Antibody to be tested 18H11H2L2 (concentration 1.5 mg/ml);

(3) After 24 hours, the cell supernatant was taken for IL-6 detection, and quantitative detection was performed with an ELISA kit (Daktronics), and the specific operation was carried out in accordance with the kit instructions.

Figure 12:
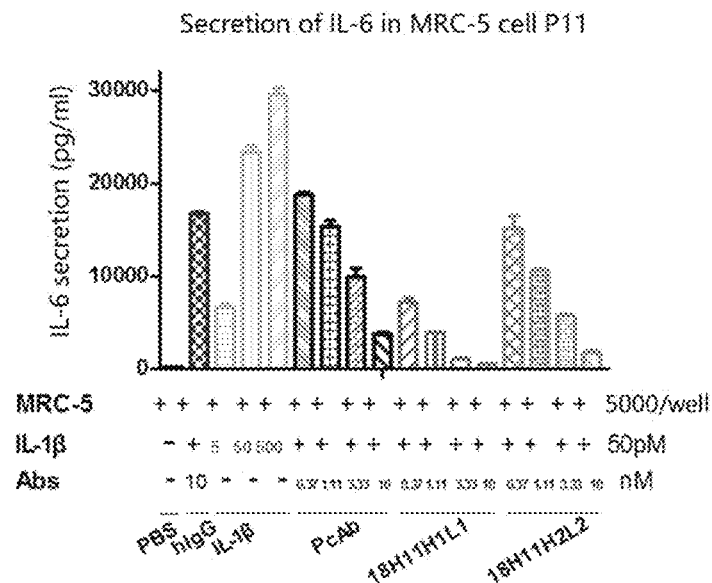
FIG. 12 shows the results of the inhibition of the humanized antibodies on IL1β-induced IL-6 secretion in MRC5 cells.

The detection results of IL-6 are shown in FIG. 12. The experimental results indicate that IL-1β can induce MRC-5 cells to secrete IL-6, and the antibodies 18H11H1L1 and 18H11H2L2 can effectively block the process of IL-1β stimulating MRC-5 cells to secrete IL-6. Among them, the inhibition effect of the antibody 18H11H1L1 on the 1LIP-induced IL6 secretion in cells is better than that of the positive control antibody, and the antibody 18H11H2L2 is equivalent to the positive control antibody.

6.4 Detection of Affinity of Humanized Antibody 18H11H1L1 (Fortebio Kinetics)

The affinity of antibody to IL1β was detected using Fortebio Octet Qke molecular interaction instrument, and the AR2G sensor was activated by EDC/sulfo-NHS for 300 s. 5 μg/mL of antibody (10 mM sodium acetate, pH 6.0 diluted) was immobilized on the surface of the sensor for 300 s. The sensor was blocked with 1M ethanolamine, pH 8.5, for 300 s. The sensor was equilibrated in PBST buffer for 300 s. The antibody immobilized on the sensor bound to IL1β-his, with the concentration of IL1β-his being 1.56-100 nM (two-fold gradient dilutions using PBST) for 300 s. The antigen and antibody were dissociated in PBST buffer for 600 s. The data was analyzed by a 1:1 model fitting, to obtain the affinity constant.

The experimental results are shown in Table 7. The results indicate that the affinity of the humanized antibody 18H11H1L1 is better than that of the positive control antibody.

TABLE 7

Affinity results of humanized antibody 18H11 H1L1

| Antibody name | KD (M) | kon (1/Ms) | kon Error | kdis (1/s) | kdis Error | Rmax (nM) |
|---|---|---|---|---|---|---|
| KF021ZP4 18H11 H1L1 | 1.42E−10 | 3.36E+05 | 3.79E+03 | 4.78E−05 | 5.44E−06 | 0.1380-0.1905 |
| KF021ZP4 PCAB | 1.79E−10 | 5.89E+05 | 7.84E+03 | 1.05E−04 | 5.97E−06 | 0.1289-0.1756 |

Example 7 In Vivo Pharmacological Study of Humanized Antibody

This experiment is intended to detect the therapeutic effect of the humanized antibody 18H11H1L1 and the murine antibody 18H11 on a mouse model of knee arthritis induced by *Lenti*-IL-1β-NIH/3T3.

Figure 13:
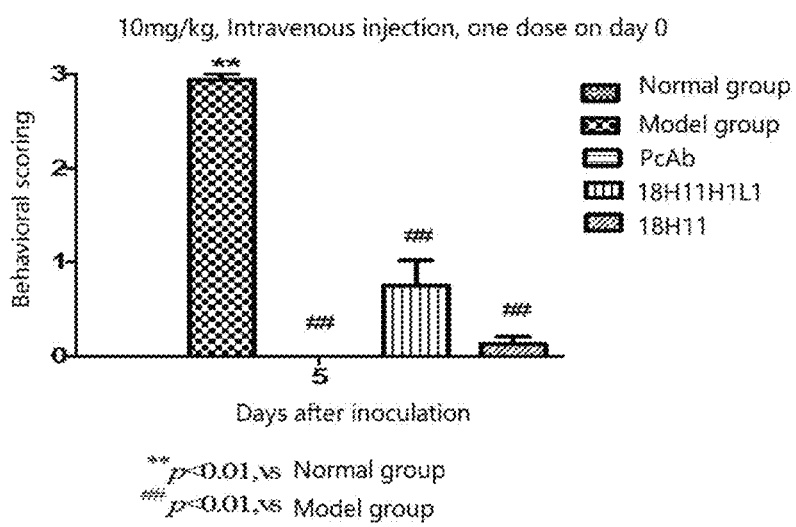
FIG. 13 shows the effects of the antibodies that bind to human IL-1β, 18H11 H1L1 and 18H11, on the pathological behavior of mice in the mouse knee arthritis model induced by Lenti-IL-1-NIH/3T3.
Figure 14:
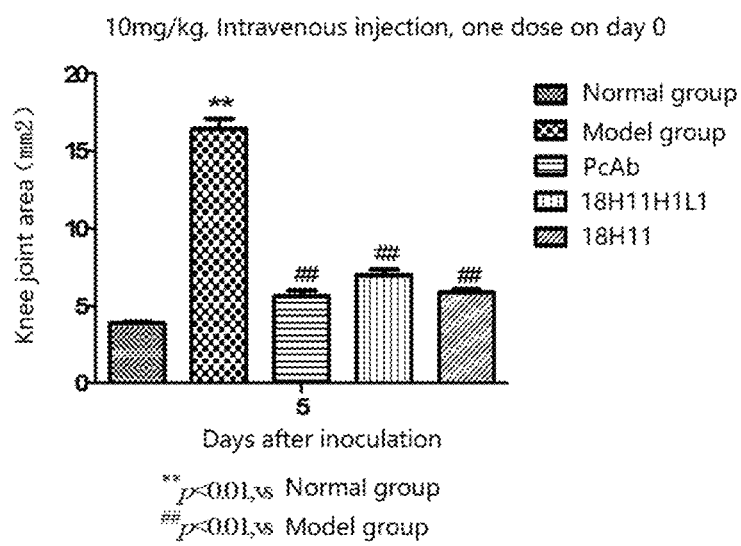
FIG. 14 shows the effects of the antibodies that bind to human IL-1β, 18H11H1L1 and 18H11, on the mouse knee joint area in the mouse knee arthritis model induced by Lenti-IL-1β-NIH/3T3.

Main Materials
1) Experimental Animals
Balb/c mice; grade: SPF; age: 5-7 weeks; sex: female: weight: 15-20 g; number: 40; source: Guangdong Medical Laboratory Animal Center: animal quality certificate number 44007200032490.
2) Cells
NIH/3T3: Source: ATCC: Cell passage: 24th passage.
*Lenti*-IL-1β-NIH/3T3: Source: Akesobio: Cell passage: 21st passage.
3) Antibodies
Negative control: Anti-HEL (Akesobio)
Positive control: PcAb
Candidate antibodies: 18H11H L1, 18H11
Sodium chloride injection (Guangdong Litai Pharmaceutical Co., Ltd.)
Experimental Methods
1) Cell Culture
The NIH3T3 (P19) and *Lenti*-IL-1β-NIH/3T3 (P16) cells were taken out from the liquid nitrogen, and quickly thawed and recovered in a 37° C. water bath. The cell suspension was added to DMEM complete medium (Gibco) containing 10% FBS (Gibco) and 1% Pen/Strep (Gibco), and cultured in a 37° C., 5% $CO_2$ incubator; then. NIH/3T3 and *Lenti*-IL-1β-NIH/3T3 were subcultured according to conventional cell culture methods, and *Lenti*-IL-1β-NIH/3T3 cells were screened by adding Blasticidin S HCl (Gibco) for each passage.
2) IL-1β Detection
The IL-1β concentration in *Lenti*-IL-1β-NIH/3T3 cell supernatant was detected according to the instructions of Human 1L-1β Precoated ELISA kit (Shenzhen Dakwei Bioengineering Co., Ltd.).
3) Grouping and Administration
Animal grouping: 40 Balb/c mice were weighed and randomly divided into 5 groups, namely Normal group, Isotype Control group, PcAb group. 18H11H1L1 group, 18H11 group, 8 mice in each group.
Dosage design: administration dose: 10 mg/kg: administration volume: 10 mlkg; administration concentration: 1 mg/ml; administration route: by tail vein injection: administration frequency: once, administered before inoculation.
Drug Preparation:
Model group: 0.490 ml of Anti-HEL (4.9 mg/ml) was accurately measured and diluted with 1.91 ml of normal saline for use;
PcAb group: 0.505 ml of KF021ZP4 PcAb (4.75 mg/ml) was accurately measured and diluted with 1.895 ml of normal saline for use;
18H11H L1 group: 0.759 ml of KF021ZP4 18H11H1L1 (3.16 mg/ml) was accurately measured and diluted with 1.641 ml of normal saline for use;
18H11 group: 0.712 ml of KF021ZP4 18H11 (3.37 mg/ml) was accurately measured and diluted with 1.688 ml of normal saline for use;
Animal administration: Before the cell inoculation, according to the body weight of the mice, the model group was injected with Anti-HEL, the PcAb group was injected with PcAb, the 18H11H1L1 group was injected with 18H11H1L1, the 18H11 group was injected with 18H11, and the normal group was injected with an equal volume of normal saline.
4) Cell Collection
When NIH/3T3 and *Lenti*-IL-1β-NIH/3T3 cells reached the required number for inoculation, the cells were collected (the cell density should not exceed 80% of the culture flask area). In the biological safety cabinet, the old medium was aspirated. After washing with PBS once, an appropriate amount of 0.05% Trypsin-EDTA (1×) (Gibco) was added for digestion at room temperature for 1 min, and then DMEM complete medium containing 10% FBS was added to stop digestion. The cell suspension was centrifuged at 1200 rpm/min for 4 min to remove the supernatant, resuspended in serum-free DMEM medium and counted, the cell concentration was adjusted to 2 million/ml, and placed on ice for use.
5) Modeling (Cell Inoculation)
After the mice were anesthetized, the normal group was inoculated with NIH/3T3 cells into the right knee joint cavities of the mice, 25 µl/mouse, namely, inoculated with 50,000 cells/mouse, and the remaining groups were inoculated with *Lenti*-IL-1β-NIH/3T3 cells into the right knee joint cavities of the mice, 25 µl/mouse, namely, inoculated with 50,000 cells/mouse. After inoculation, the wound at the knee joint was sutured and wiped with penicillin that was diluted 20 fold to prevent wound infection.
6) Behavioral Scoring and Knee Joint Area Measurement
On the 5th day after cell inoculation, the mice in each group were scored behaviorally. Behavioral scoring criteria: Score 0: the mouse has normal activity and can move bilaterally; Score 1: the mouse walks abnormally and can move bilaterally; Score 2: the affected limb of the mouse touches the ground briefly and can move bilaterally; Score 3: the affected limb of the mouse cannot touch the ground and moves unilaterally. After scoring, the mice in each group were euthanized and the length (mm) and width (mm) of the synovial membrane of the knee joint of the mouse's affected limb were measured with a vernier caliper, to calculate the knee joint area ($mm^2$).
7) Experimental Statistical Analysis Methods
The data were described as mean±standard deviation ($\overline{X}$±S). The comparison between groups was processed by GraphPad statistical software, and then the results were evaluated by one-way analysis of variance. $P<0.05$: a significant difference, $P<0.01$: a very significant difference.
Experimental Results
1) Behavioral Scoring of Antibodies 18H11H1L1, 18H11 in Mice
See FIG. 13. Compared to the normal group, the pathological abnormalities of the mice in the model group increased significantly ($P<0.01$). After drug administration, the positive drug group (PcAb group), 18H11H1L1 group and 18H11 group can effectively inhibit the abnormal walking behavior of the affected limb of mice ($P<0.01$); the efficacy of 18H11H1L1 and 18H11 was equivalent to that of the positive drug.
2) Effect of Antibodies 18H11 HIL and 18H11 on the Area of the Knee Joint in Mice
See FIG. 14. Compared to the normal group, the knee joint area of mice in the model group increased significantly ($P<0.01$), and the knee joints were swollen. After drug administration, the positive drug group (PcAb group), 18H11H1L1 group and 18H11 group can effectively inhibit the swelling area of the knee joints of the affected limbs of mice ($P<0.01$); the efficacy of 18H11 HL 1 and 18H11 was equivalent to that of the positive drug.

The results of this experiment show that in the knee arthritis model established by *Lenti*-IL-1I$-NIH/3T3, the three antibodies of PcAb, 18H11H1L1 and 18H11 at a dose of 10 mg/kg can significantly improve the walking behavior of the affected limbs of mice and significantly reduce the swelling area of the knee joints of the affected limbs; the efficacy of the 18H11H1L1 and 18H11 antibody is equivalent to that of the positive drug.

Example 8 Preparation of Mutant Antibody

Figure 15:
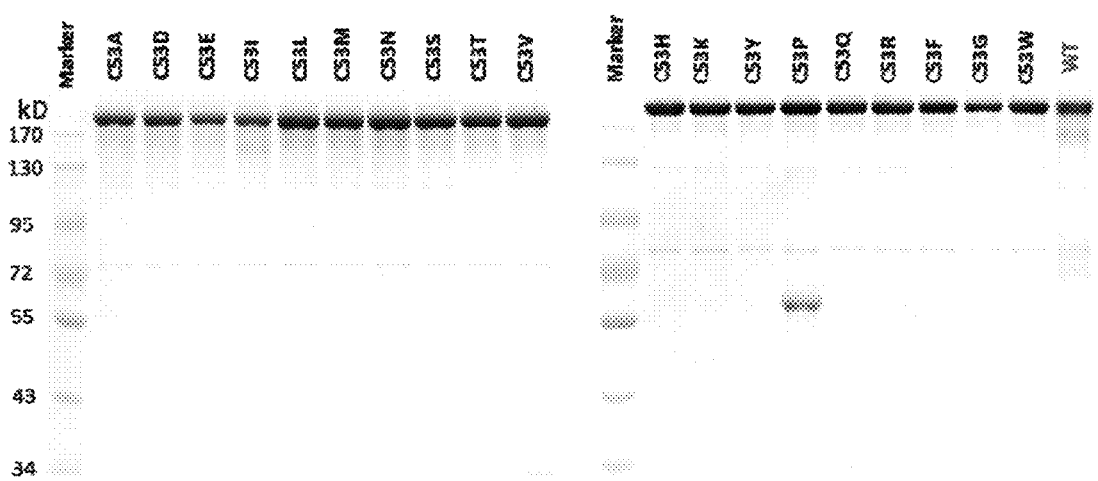
FIG. 15 shows the results of SDS-PAGE protein electrophoresis of each mutant antibody.

Using the heavy chain of 18H11H1L1 as a template, primers were designed to perform PCR to mutate cysteine at position 53 (C, located in the heavy chain complementarity determining region H-CDR2) of the heavy chain to alanine (A), valine (V), leucine (L), isoleucine (I), methionine (M), phenylalanine (F), asparagine (N), glutamate (E), glutamine (Q), histidine (H), lysine (K), arginine (R), aspartate (D), glycine (G), serine (S), threonine (T), tyrosine (Y), tryptophan (W), proline (P), respectively. 0.5 µL of Dpn I enzyme (New England BioLabs, Cat #R0176L) was added to the reaction system after PCR, reacted at 37° C. for 30 min for digestion template, placed on ice for 5 min after the completion of digestion, and subjected to transformation. The next day, the bacteria were picked, sequenced, and clones with the correct mutation were selected and co-transfected with the light chain of 18H1 1 H1L1 into 293-F cells. After 7 days, the culture solution was centrifuged at high-speed, vacuum filtered through a microporous membrane, and purified by a Protein A column according to the operating method provided by the manufacturer, to obtain each mutant antibody. The results of SDS-PAGE protein electrophoresis of each mutant antibody are shown in FIG. 15, WT is 18H11H1L1.

Example 9 Detection of Affinity of Mutant Antibody (ELISA)

Referring to the method in Example 6.1, the detection of binding affinity of each mutant antibody to antigen IL1β was carried out.

Figure 16:
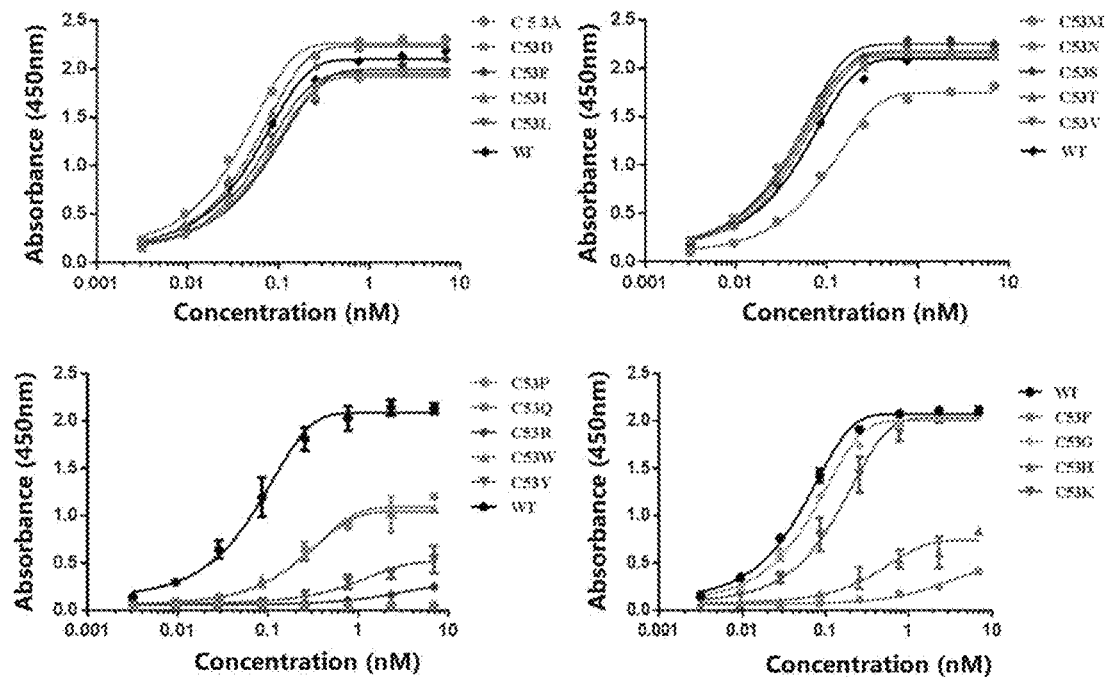
FIG. 16 shows the $EC_{50}$ of binding affinity of each mutant antibody and 18H11 H1L1 (WT) to IL1β.

The $EC_{50}$ of each mutant antibody and 18H11H1 L1 (WT) for binding to IL0 is shown in FIG. 16 and the corresponding table, respectively.

Example 10 Detection of Inhibition of Mutant Antibody on IL-1β-Induced IL-6 Secretion in Cells Referring to Example 6.3 for the experimental methods. Based on the experimental results of Example 9, the antibodies with good binding affinity to IL-1β were selected, to determine their inhibitory activity on 1L-1β-induced IL-6 secretion in MRC-5 cells.

Figure 17:
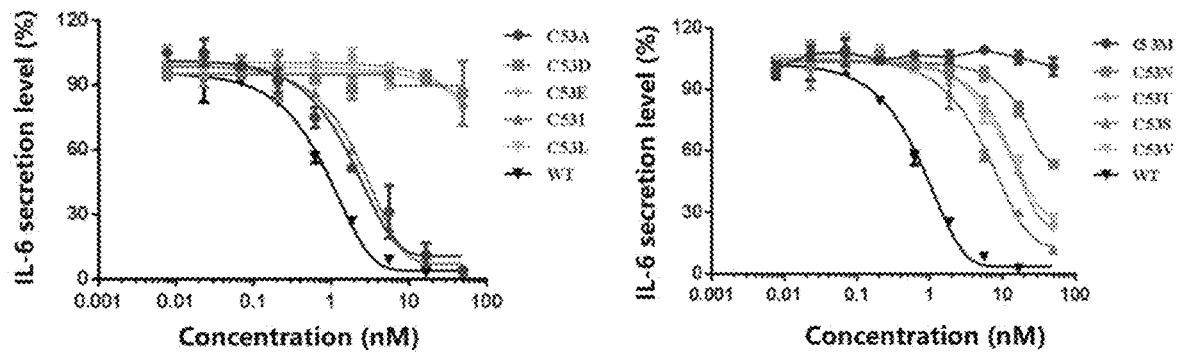
FIG. 17 shows the inhibitory activity of the antibodies on IL-1β-induced IL-6 secretion in MRC-5 cells.

As shown in FIG. 17, the results indicate that compared to other mutant antibodies, 18H11-Hu-C53I (i.e., C53I) and 18H11-Hu-C53A (i.e., C53A) have better inhibitory activity on IL-1β-induced IL-6 secretion in MRC-5 cells, with an $IC_{50}$ of 2.416 nM and 2.323 nM, respectively.

Example 11 Detection of Thermal Stability of Mutant Antibody

The samples of 18H11-Hu-C53I, 18H11-Hu-C53A and 18H11H1L1 were placed in a 40° C. water bath for 28 days, and samples were taken at different time points. After taking the samples at the last time point, the binding affinity of each sample to 1L-10 and the inhibitory activity on IL-1l-induced IL-6 secretion in MRC-5 cells were determined according to experimental methods in Examples 6.1 and 6.3, respectively.

Figure 18:
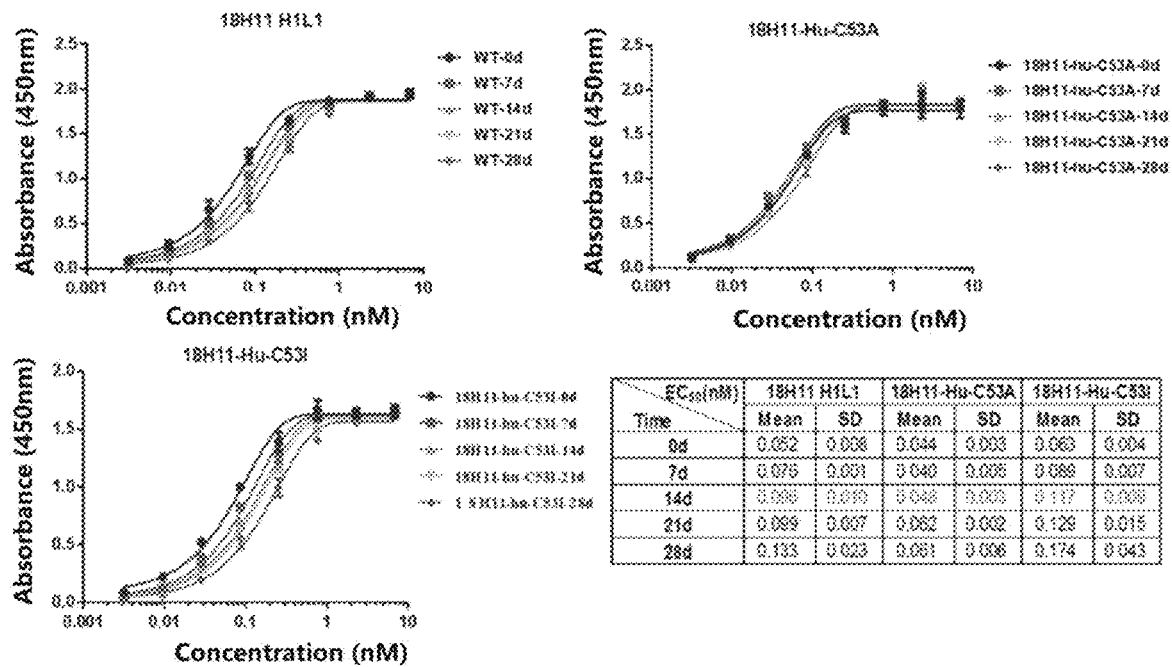
FIG. 18 shows the binding affinity of each sample to IL-1β.

The results are shown in FIG. 18, and the $EC_{50}$ of each sample is shown in the table of the figure. It is known that when the samples were placed in a 40° C. water bath, from 0 d to 28 d, the binding affinity of 18H11H1L1 to IL-1β attenuated by about 2.6 times, the binding affinity of 18H11-Hu-C53A attenuated by about 1.4 times, the binding affinity of 18H11-Hu-C53I attenuated by about 2.7 times.

Figure 19:
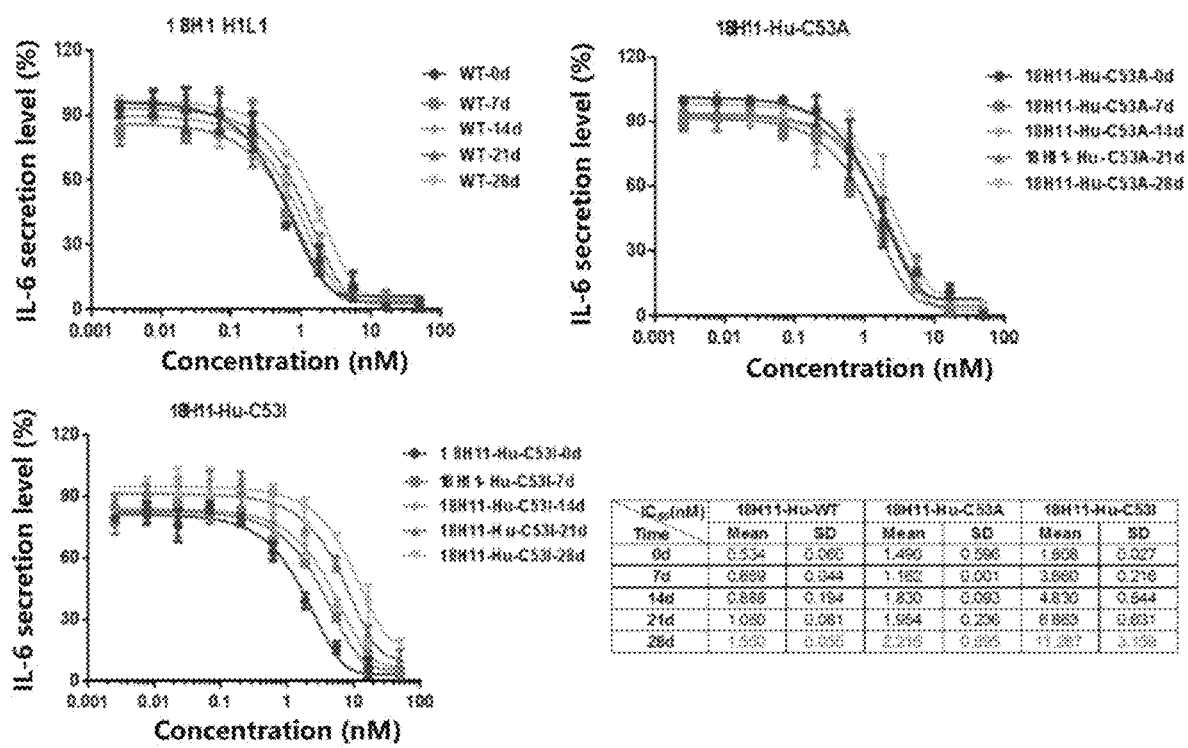
FIG. 19 shows the inhibitory activity of each sample on IL-1β-induced IL-6 secretion in MRC-5 cells.

As shown in FIG. 19, the results indicate that when 18H11-Hu-C53I, 18H11-Hu-C53A and 18H11H1L1 (i.e., 18H11-Hu-WT) were placed in a 40° C. water bath, from 0 d to 28 d, the inhibitory activity of 18H11H1L1 on IL-1R-induced IL-6 secretion in MRC-5 cells decreased about 2.9 times, the inhibitory activity of 18H11-Hu-C53I decreased about 6.2 times, and the inhibitory activity of 18H11-Hu-C53A decreased about 1.5 times. The $IC_{50}$ of each sample is shown in the table of the figure.

In summary, the relative thermal stability of 18H11-Hu-C53A is better than that of 18H11H L1 and 18H11-Hu-C53I.

Example 12 Detection of Affinity of 18H11-Hu-C53A Competing with IL1RI for Binding to Antigen IL1β

Referring to the method in Example 6.2, the affinity detection of the mutant antibody 18H11-Hu-C53A competing with IL1RI for binding to antigen IL1β was carried out.

Figure 20:
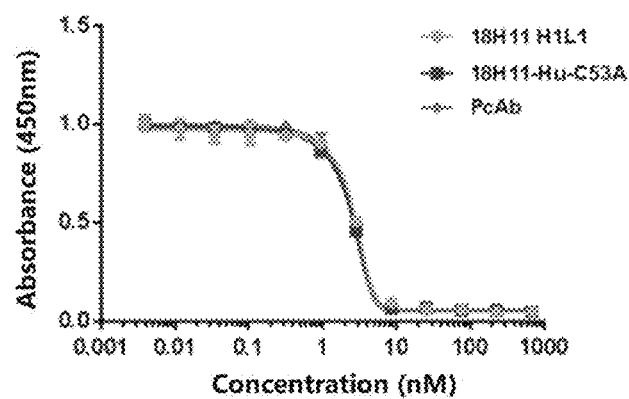
FIG. 20 shows the activity of 18H11-Hu-C53A competing with IL1RI for binding to antigen IL1β.

As shown in FIG. 20, the $IC_{50}$s of 18H11 HIL1, 18H11-Hu-C53A and PCAb for blocking the binding of IL10 to IL1RI were 0.028 nM, 0.028 nM and 0.030 nM, respectively, indicating that 18H11-Hu-C53A can also effectively block the binding of IL110 to IL1RI, and its activity is equivalent to that of 18H11H1L1 and the positive control antibody PCAb.

Example 13 Detection of Affinity of 18H11-Hu-C53A (Biacore)

The binding kinetic parameters of 18H11 HIL1, 18H11-Hu-C53A and PCAb to IL1β were measured by Biacore, and the method was as follows: using the capture method, 0.5 µg/mL of antibody was captured on a ProteinA chip (purchased from GE, Lot No. 10261132). Set: contact time 75 s, flow rate 10 L/min, regeneration contact time 30s. The antigen was used as an analyte; Set: contact time 180 s, dissociation time 900 s, flow rate 30 L/min, regeneration contact time 30 s. The detected results of the kinetic parameters are shown in Table 8.

TABLE 8

| Affinity results of mutant antibody 18H11-Hu-C53A | | | |
|---|---|---|---|
| Sample | ka (1/Ms) | kd (1/s) | KD (M) |
| PcAb | 1.69E+06 | 1.04E−04 | 6.16E−11 |
| 18H11 H1L1 | 8.18E+05 | 8.12E−05 | 9.93E−11 |
| 18H11-Hu-C53A | 5.59E+05 | 9.81E−05 | 1.75E−10 |

Example 14 Determination of In Vivo Drug Efficacy of 18H11-Hu-C53A

The Balb/c female mice (5-7 weeks old, 15-20 g) that were adaptively cultured for one week were divided into 7 groups according to the body weight, 8 mice in each group; injected intraperitoneally with the antibody 18H11-Hu- C53A according to the following dosage: 2.5 mg/kg, 0.5 mg/kg, 0.1 mg/kg, and the control group was injected with PBS or isotype control IgG. 24 hours after the antibody injection, each mouse was injected subcutaneously with 5 μg of recombinant human IL-1β-His: 4 hours after the IL-1β injection, blood was collected from each group of mice; serum was separated at 4° C., and the expression level of murine IL-6 in serum was detected by ELISA to determine the inhibitory effect of different doses of antibody on IL-6 secretion in mice.

Figure 21:
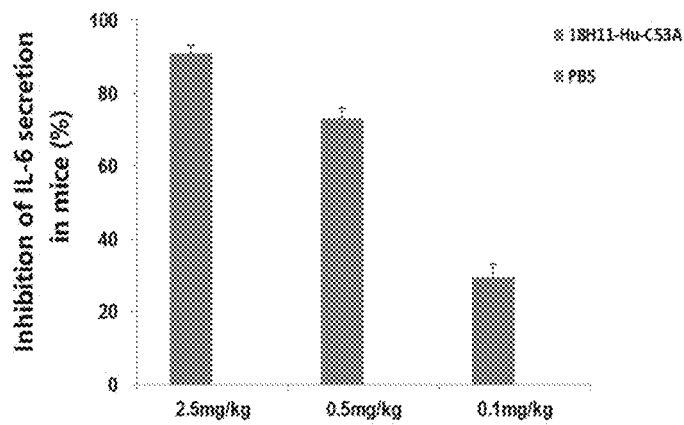
FIG. 21 shows the inhibitory effect of different doses of antibodies on IL-6 secretion in mice.

The results are shown in FIG. 21. Compared to the PBS group (negative control group, PBS was used as a control, the actual value was 0), 18H11-Hu-C53A had an inhibitory rate of as high as 91.06% on IL-6 secretion in mice when used at a dose of 2.5 mg/kg, an inhibitory rate of 73.11% on IL-6 secretion in mice at a dose of 0.5 mg/kg, and an inhibitory rate of 29.46% on IL-6 secretion in mice at a dose of 0.1 mg/kg.

Example 15 Determination of Cross-Species Immunoreactivity of 18H11-Hu-C53A

In this example, the cross-species immunoreactivity of 18H11-Hu-C53A was determined by ELISA.

A 96-well ELISA plate was coated with macaque IL-1β protein (*Macaca*-IL-1β protein, NCBI Reference Sequence: NP_001270498.1) and rat IL-1β protein (Rat-IL-1β, NCBI Reference Sequence: NP_113700.2) at 0.2 μg/well to determine the cross-reactivity of 18H11-Hu-C53A to IL-1β of these two species. The experimental methods refer to Example 6.1 and the preparation methods of *Macaca*-IL-1β and Rat-IL-1β proteins refer to Example 1.1.

Figure 22:
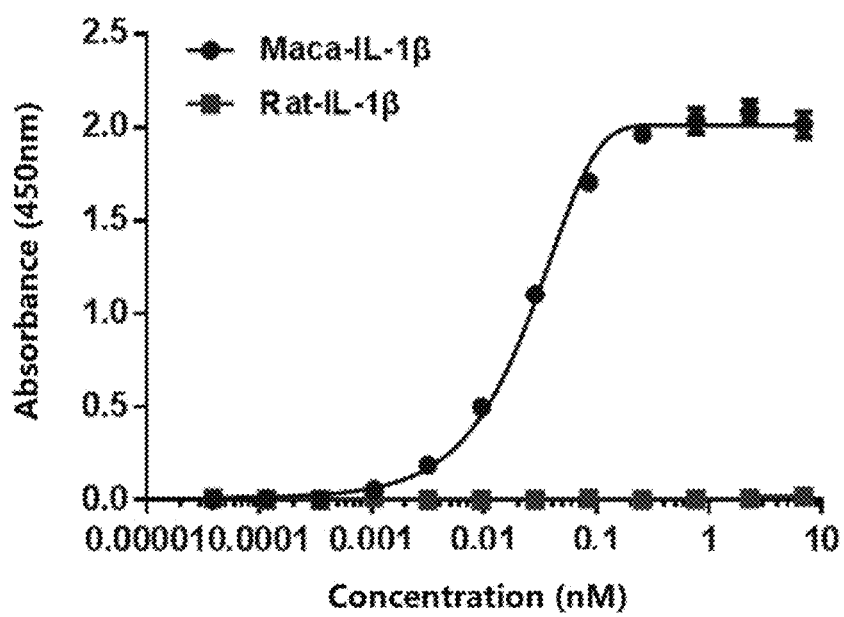
FIG. 22 shows the cross reaction of 18H11-Hu-C53A in different species determined by ELISA.

The results are shown in FIG. 22, indicating that 18H11-Hu-C53A can well recognize macaque IL-1β protein with an $EC_{50}$ of 0.025 nM, but can not recognize rat IL-1β0 protein.

Example 16 Determination of the Selectivity of 18H11-Hu-C53A to Family Member Proteins IL-1 Alpha, IL-1 R2 and IL-1 RA A 96-well ELISA plate was coated with human IL-1 alpha, IL-1 R2 and IL-1 RA proteins (all purchased from Sino Biological Company. Catolog Nos.: 10128-HNCH-20, 10111-H08H-50 and 10123-HNAE-100, respectively) at 0.2 μg/well to determine the selectivity of 18H11-Hu-C53A to these proteins. The other specific experimental methods refer to Example 6.1.

Figure 23:
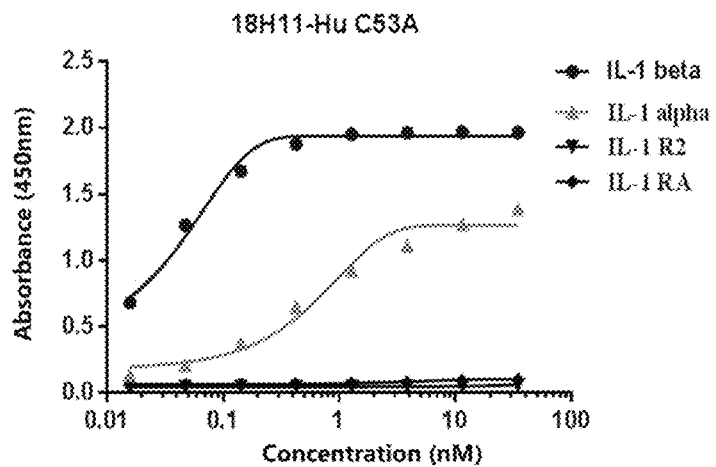
FIG. 23 shows the selectivity of 18H11-Hu-C53A to family member proteins IL-1 alpha, IL-1 R2 and IL-1 RA.

The results are shown in FIG. 23, indicating that 18H11-Hu-C53A has no cross-reactivity to IL-1 R2 and IL-1 RA. The $EC_{50}$ for IL-1α (IL-1 alpha) was 0.652 nM, and the $EC_{50}$ for IL-1β (IL—1beta) was 0.026 nM. These results indicate that 18H11-Hu-C53A can specifically recognize human IL-1β.

Example 17 Determination of the Epitopes of that 18H11-Hu-C53A Binds to IL-1β

According to the spatial structure. IL-1β (positions 1-153 of SEQ ID NO: 23) was divided into two protein fragments for expression and purification, namely IL-1s-A1-F99-His (alanine A at position I to phenylalanine F at position 99, with a 6-His tag at the C-terminus) and IL-1β-A1-W120-His (alanine A at position I to tryptophan W at position 120, with a 6×His tag at the C-terminus). IL-1β-A1-F99-His, IL-1β-A1-W120-His and IL-1β-WT-His (i.e., IL-1β-his) were diluted to 0.5 μg/mL with the coating solution to coat the ELISA plate. The affinity of 18H11-Hu-C53A to each protein was determined referring to Example 6.1.

Figure 24:
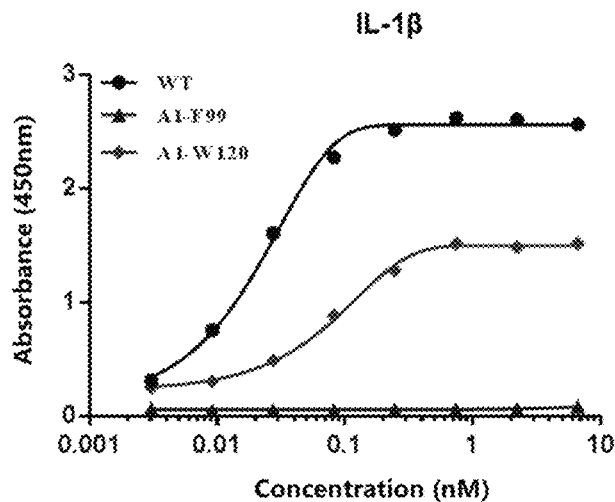
FIGS. 24-27 show the binding epitopes of 18H11-Hu-C53A to IL-1β.

As shown in FIG. 24, the results indicate that 18H11-Hu-C53A does not bind to IL-1β-A1-F99-His at all, while has a certain affinity for IL-1β-A1-W120-His, however, the affinity is lower than that to IL-1β-WT-His. Thus, primers were designed to perform single point mutation one by one through Alanine scanning on the amino acids between the 99th amino acid F and the 120th amino acid W of IL-1β and the other amino acids near the latter, and then the single point mutation proteins were expressed and purified. The binding epitope for 18H11-Hu-C53A was determined, referring to the methods described above.

Figure 25:
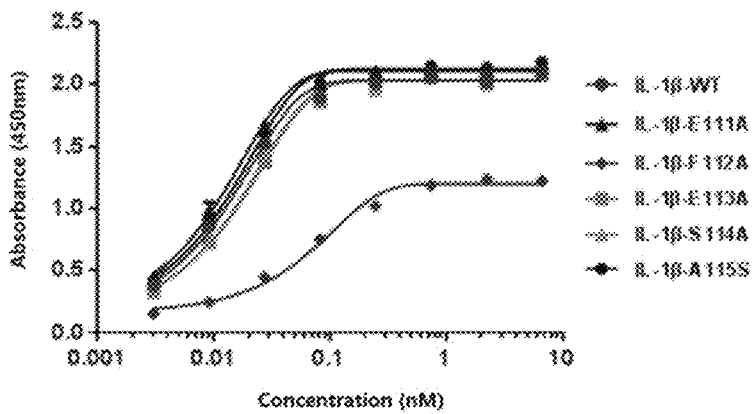
Figure 26:
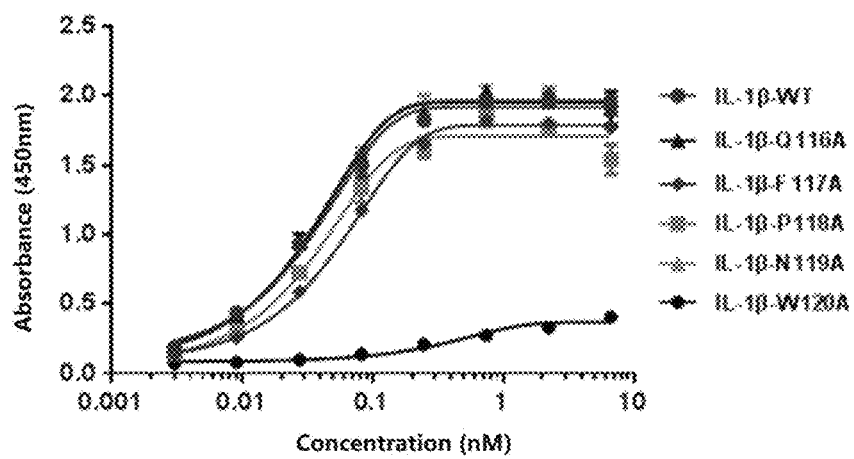
Figure 27:
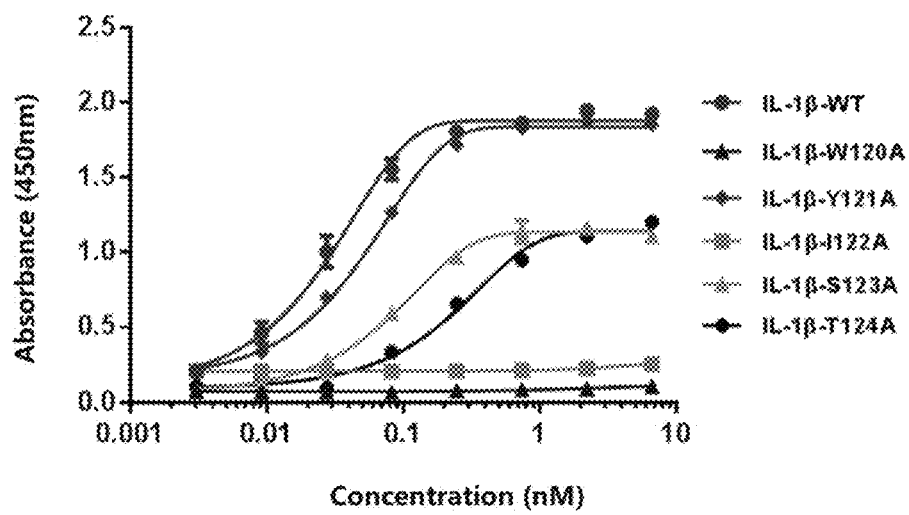

Representative experimental results are shown in FIG. 25, FIG. 26, and FIG. 27, respectively. It can be seen that the amino acids that have the greatest impact on the binding of 18H11-Hu-C53A to IL-1β, namely the main binding epitopes comprise tryptophan W at position 120 and isoleucine I at position 122, and then phenylalanine F at position 112, serine S at position 123, and threonine T at position 124.

What is claimed is:

1. An antibody or antigen-binding fragment thereof that binds to human IL-1β, characterized in that, the antibody or antigen-binding fragment thereof comprises:
   (1) heavy chain complementarity determining regions H-CDR1, H-CDR2, H-CDR3, wherein the H-CDR1 having the amino acid sequence as shown in SEQ ID NO: 1, the H-CDR2 having the amino acid sequence as shown in SEQ ID NO: 2, and the H-CDR3 having the amino acid sequence as shown in SEQ ID NO: 3, and
   (2) light chain complementarity determining regions L-CDR1, L-CDR2, L-CDR3, wherein the L-CDR1 having the amino acid sequence as shown in SEQ ID NO: 4, the L-CDR2 having the amino acid sequence as shown in SEQ ID NO: 5, and the L-CDR3 having the amino acid sequence as shown in SEQ ID NO: 6.

2. The antibody or antigen-binding fragment thereof that binds to human IL-1β according to claim 1, characterized in that, the antibody is a murine antibody or a humanized antibody.

3. The antibody or antigen-binding fragment thereof that binds to human IL-1β according to claim 2, characterized in that, the antibody is a murine antibody, comprising a heavy chain variable region having the amino acid sequence as shown in SEQ ID NO: 7, and a light chain variable region having the amino acid sequence as shown in SEQ ID NO: 8.

4. The antibody or antigen-binding fragment thereof that binds to human IL-1β3 according to claim 2, characterized in that, the antibody is a humanized antibody, comprising a heavy chain variable region having the amino acid sequence as shown in one of SEQ ID NO: 9, SEQ ID NO: 11 or SEQ ID NO: 13, and a light chain variable region having the amino acid sequence as shown in one of SEQ ID NO: 10, SEQ ID NO: 12 or SEQ ID NO: 14.

5. The antibody or antigen-binding fragment thereof that binds to human IL-1β according to claim 1, characterized in that, the antigen-binding fragment comprises a Fab fragment, a F(ab)'2 fragment, a Fv fragment, or a single chain antibody.

6. An antibody or antigen-binding fragment thereof that binds to human IL-1β, characterized in that, the antibody or antigen-binding fragment thereof comprises: (1) heavy chain complementarity determining regions H-CDR1, H-CDR2, H-CDR3, wherein the H-CDR1 having the amino acid sequence as shown in SEQ ID NO: 1, the H-CDR2 having the amino acid sequence as shown in SEQ ID NO: 38, and the H-CDR3 having the amino acid sequence as shown in SEQ ID NO: 3, and (2) light chain complementarity determining regions L-CDR1, L-CDR2, L-CDR3, wherein the L-CDR1 having the amino acid sequence as shown in SEQ ID NO: 4, the L-CDR2 having the amino acid sequence as shown in SEQ ID NO: 5, and the L-CDR3 having the amino acid sequence as shown in SEQ ID NO: 6.

7. A nucleic acid molecule, characterized in that, the nucleic acid molecule encodes the antibody or antigen-binding fragment thereof that binds to human IL-1β according to claim 1.

8. The nucleic acid molecule according to claim 7, characterized in that, the nucleic acid molecule has the nucleotide sequence encoding the heavy chain variable region as shown in one of SEQ ID NO: 15, SEQ ID NO: 17, SEQ ID NO: 19 or SEQ ID NO: 21, and the nucleotide sequence encoding the light chain variable region as shown in one of SEQ ID NO: 16, SEQ ID NO: 18, SEQ ID NO: 20 or SEQ ID NO: 22.

9. An expression vector, characterized in that, the expression vector comprises the nucleic acid molecule according to claim 7.

10. A host cell, characterized in that, the host cell comprises the expression vector according to claim 9.

11. A method for preparing an antibody or antigen-binding fragment thereof that binds to human IL-1β, characterized in that, the method comprises the following steps of:
   a) under expression conditions, culturing the host cell according to claim 10, to express the antibody or antigen-binding fragment thereof that binds to human IL-1β;
   b) isolating and purifying the antibody or antigen-binding fragment thereof that binds to human IL-1β of step a).

12. A pharmaceutical composition, characterized in that, the pharmaceutical composition comprises the antibody or antigen-binding fragment thereof that binds to human IL-1β according to claim 1, and a pharmaceutically acceptable carrier.

13. A method for treating an immune disease caused by IL-1β overexpression comprising: administering to an individual in need thereof an antibody or antigen-binding fragment thereof that binds to human IL-1β according to claim 1.

14. The method according to claim 13, characterized in that, the immune disease caused by IL-1β overexpression is arthritis, osteoporosis or psoriasis.

* * * * *